(12) United States Patent
Laufer

(10) Patent No.: US 9,277,921 B2
(45) Date of Patent: *Mar. 8, 2016

(54) GASTROINTESTINAL IMPLANT AND METHODS FOR USE

(71) Applicant: Michael D. Laufer, Menlo Park, CA (US)

(72) Inventor: Michael D. Laufer, Menlo Park, CA (US)

( * ) Notice: Subject to any disclaimer, the term of this patent is extended or adjusted under 35 U.S.C. 154(b) by 270 days.

This patent is subject to a terminal disclaimer.

(21) Appl. No.: 13/768,573

(22) Filed: Feb. 15, 2013

(65) Prior Publication Data

US 2013/0178879 A1     Jul. 11, 2013

Related U.S. Application Data

(63) Continuation of application No. 12/645,378, filed on Dec. 22, 2009, now Pat. No. 8,376,981, which is a continuation-in-part of application No. 12/203,030, filed on Sep. 2, 2008, now Pat. No. 8,118,767, which is a continuation of application No. PCT/US2007/063140, filed on Mar. 2, 2007.

(60) Provisional application No. 60/779,062, filed on Mar. 2, 2006.

(51) Int. Cl.
| | |
|---|---|
| *A61B 19/00* | (2006.01) |
| *A61B 17/11* | (2006.01) |
| *A61F 5/00* | (2006.01) |
| *A61F 2/07* | (2013.01) |
| *A61F 2/24* | (2006.01) |
| *A61F 2/91* | (2013.01) |
| *A61F 2/06* | (2013.01) |
| *A61F 2/30* | (2006.01) |

(52) U.S. Cl.
CPC ........... *A61B 17/1114* (2013.01); *A61F 5/0076* (2013.01); *A61F 2/07* (2013.01); *A61F 2/24* (2013.01); *A61F 2/91* (2013.01); *A61F 2002/068* (2013.01); *A61F 2002/30329* (2013.01); *A61F 2220/0025* (2013.01); *A61F 2250/0039* (2013.01)

(58) Field of Classification Search
CPC ............. A61B 17/1114; A61B 5/0076; A61B 2200/0025
USPC ................................ 604/8, 9, 264; 623/23.68
See application file for complete search history.

(56) References Cited

U.S. PATENT DOCUMENTS

| | | |
|---|---|---|
| 3,818,511 A | 6/1974 | Goldberg |
| 4,134,405 A | 1/1979 | Smit |

(Continued)

FOREIGN PATENT DOCUMENTS

| | | |
|---|---|---|
| WO | WO 2004/087233 | 10/2004 |
| WO | WO 2005/037073 | 4/2005 |
| WO | WO 2007/050628 | 5/2007 |

OTHER PUBLICATIONS http://en.wikipedia.org/wiki/Nitinol (online encyclopedia, accessed Oct. 7, 2010).

(Continued)

*Primary Examiner* — Leslie Deak
(74) *Attorney, Agent, or Firm* — Levine Bagade Han LLP

(57) ABSTRACT

Methods and devices for modifying the location at which bodily fluids interact with nutrients in a gastrointestinal tract. The methods and devices utilize a conduit configured to divert bodily fluids from an entrance within a gastrointestinal tract to a location downstream from the entrance.

24 Claims, 14 Drawing Sheets

(56) References Cited

U.S. PATENT DOCUMENTS

| | | |
|---|---|---|
| 4,315,509 A | 2/1982 | Smit |
| 4,501,264 A | 2/1985 | Rockey |
| 4,548,201 A | 10/1985 | Yoon |
| 4,641,653 A | 2/1987 | Rockey |
| 4,648,383 A | 3/1987 | Angelchik |
| 4,681,570 A | 7/1987 | Dalton |
| 4,719,916 A | 1/1988 | Ravo |
| 4,878,905 A | 11/1989 | Blass |
| 5,306,300 A | 4/1994 | Berry |
| 5,356,416 A | 10/1994 | Chu et al. |
| 5,425,765 A | 6/1995 | Tiefenbrun et al. |
| 5,489,295 A | 2/1996 | Piplani et al. |
| 5,540,713 A | 7/1996 | Schnepp-Pesch et al. |
| 5,676,696 A | 10/1997 | Marcade |
| 5,820,584 A | 10/1998 | Crabb |
| 5,876,450 A | 3/1999 | Johlin |
| 5,904,697 A | 5/1999 | Gifford, III et al. |
| 6,117,167 A | 9/2000 | Goicoechea et al. |
| 6,132,471 A | 10/2000 | Johlin, Jr. |
| 6,543,456 B1 | 4/2003 | Freeman |
| 6,546,280 B2 | 4/2003 | Osborne |
| 6,572,629 B2 | 6/2003 | Kalloo et al. |
| 6,582,472 B2 | 6/2003 | Hart |
| 6,675,809 B2 | 1/2004 | Stack et al. |
| 6,740,121 B2 | 5/2004 | Geitz |
| 6,746,489 B2 | 6/2004 | Dua et al. |
| 6,918,871 B2 | 7/2005 | Schulze |
| 6,946,002 B2 | 9/2005 | Geitz |
| 7,025,791 B2 | 4/2006 | Levine et al. |
| 7,037,344 B2 | 5/2006 | Kagan et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,316,716 B2 | 1/2008 | Egan |
| 7,354,454 B2 | 4/2008 | Stack et al. |
| 7,476,256 B2 | 1/2009 | Meade et al. |
| 2003/0032967 A1 | 2/2003 | Park et al. |
| 2003/0040804 A1 | 2/2003 | Stack et al. |
| 2003/0065359 A1 | 4/2003 | Weller et al. |
| 2003/0069533 A1 | 4/2003 | Kakutani et al. |
| 2003/0109931 A1 | 6/2003 | Geitz |
| 2003/0199989 A1 | 10/2003 | Stack et al. |
| 2004/0039452 A1 | 2/2004 | Bessler |
| 2004/0092892 A1 | 5/2004 | Kagan et al. |
| 2004/0092974 A1 | 5/2004 | Gannoe et al. |
| 2004/0107004 A1 | 6/2004 | Levine et al. |
| 2004/0117031 A1 | 6/2004 | Stack et al. |
| 2004/0122456 A1 | 6/2004 | Saadat et al. |
| 2004/0133147 A1 | 7/2004 | Woo |
| 2004/0249362 A1 | 12/2004 | Levine et al. |
| 2005/0022827 A1 | 2/2005 | Woo et al. |
| 2005/0038415 A1 | 2/2005 | Rohr et al. |
| 2005/0043817 A1 | 2/2005 | McKenna et al. |
| 2005/0049718 A1 | 3/2005 | Dann et al. |
| 2005/0085787 A1 | 4/2005 | Laufer |
| 2005/0177181 A1 | 8/2005 | Kagan et al. |
| 2005/0187566 A1 | 8/2005 | Byrum |
| 2005/0228504 A1 | 10/2005 | Demarais |
| 2005/0256587 A1 | 11/2005 | Egan |
| 2006/0020247 A1 | 1/2006 | Kagan et al. |
| 2006/0106332 A1 | 5/2006 | Knudson et al. |
| 2006/0142787 A1 | 6/2006 | Weller et al. |
| 2006/0206063 A1 | 9/2006 | Kagan et al. |
| 2006/0206064 A1 | 9/2006 | Kagan et al. |
| 2006/0293742 A1 | 12/2006 | Dann et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0198074 A1 | 8/2007 | Dann et al. |
| 2007/0282453 A1 | 12/2007 | Weitzner et al. |
| 2007/0282454 A1 | 12/2007 | Krueger et al. |
| 2008/0269662 A1 | 10/2008 | Vassiliades et al. |
| 2009/0062717 A1 | 3/2009 | Laufer |
| 2009/0149871 A9 | 6/2009 | Kagan et al. |

OTHER PUBLICATIONS

Rudnicki et al., A Simple Method for Biliary-enteric Anastomosis and Chronic Bile Diversion in the Rat, Hepatology, Official Journal of the American Association for the Study of Liver Diseases, vol. 14, No. 1, pp. 128-130, 1991.

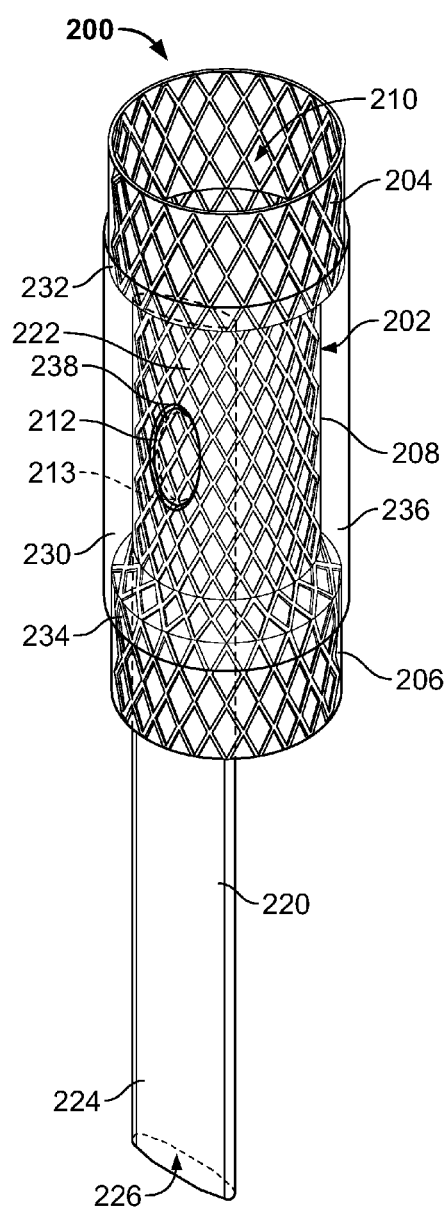
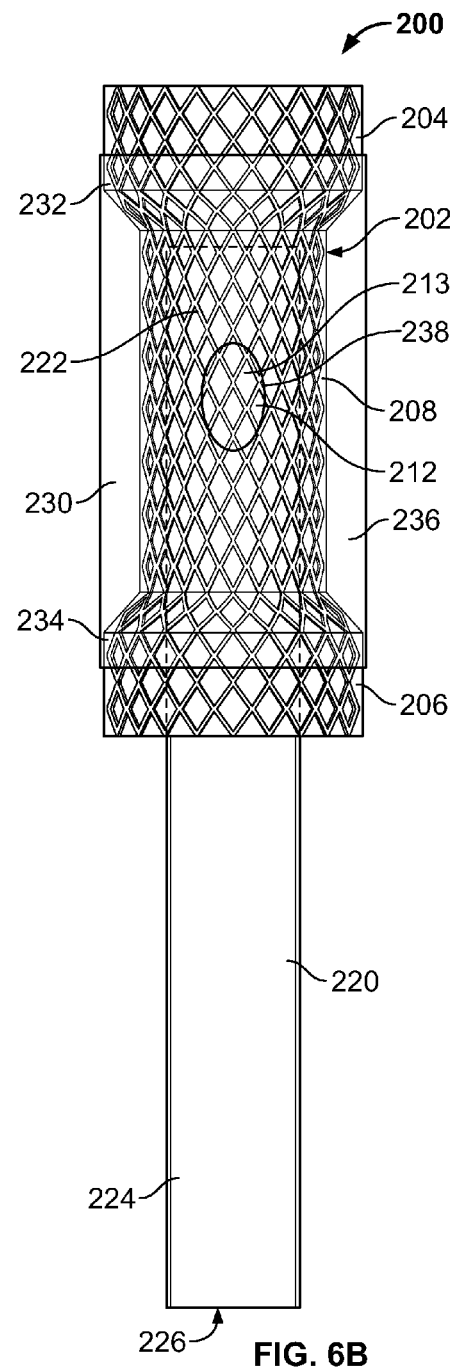
FIG. 6A
FIG. 6B

GASTROINTESTINAL IMPLANT AND METHODS FOR USE

CROSS-REFERENCE TO RELATED APPLICATIONS

This application is a continuation of U.S. patent application Ser. No. 12/645,378, filed Dec. 22, 2009, now issued U.S. Pat. No. 8,376,981, which is a continuation-in-part of U.S. patent application Ser. No. 12/203,030 filed Sep. 2, 2008, now issued U.S. Pat. No. 8,118,767, which is a continuation of PCT International Application No. PCT/US2007/063140 filed Mar. 2, 2007 which claims the benefit under 35 U.S.C. §119(e) of U.S. Provisional Application No. 60/779,062 filed Mar. 2, 2006. The contents of all of these applications are incorporated herein by reference in their entirety.

BACKGROUND OF THE INVENTION

The incidence of obesity in the United States is significantly increasing causing an associated increase in obesity-related health problems. Because of this trend, efforts to control obesity are gaining the increased attention of both the medical community and the general public. However, while there may be a considerable number of individuals that are markedly overweight, a fraction of these individuals are currently eligible for surgery to reconstruct their gastrointestinal (GI) tract in order to control their weight. These GI procedures are reserved for the severely obese because of the significant complications associated with the surgery. Because these procedures often involve invasive surgery, the recuperation time is significant not to mention the possibility of complications which include the risk of death. It is estimated that without GI reconstruction, eligible patients face an annual mortality as high as 30%-50%. Obviously such a high risk of death justifies the use of these surgical procedures. It is contemplated that less invasive procedures would be better suited for the severely obese as well as those moderately or less obese.

FIG. 1A is an illustration of the digestive system. The digestive tract is a disassembly line in which food breaks down to become less and less complex so that nutrients become available to the body. As the food passes through the digestive tract, it mixes with other fluids to create a fluid mix. Below the esophagus 16, the (GI) tract expands to form the stomach 18. In the stomach 18 mechanical and chemical breakdowns of proteins occurs such that food leaves the stomach converted into a substance called chyme. From the stomach 18, the chyme, enters the small intestine 20 where secretions from the liver 22 and the pancreas 24 complete the digestive process.

The liver 22 produces which is then stored in the gall bladder 26. Bile is a complex mixture of essentially emulsifiers and surfactants that the body uses to absorb fat. Without bile, dietary fat is relatively insoluble and would pass out of the body as feces. The pancreas produces pancreatic enzymes which the body uses to digest and absorb proteins, and to a lesser degree, carbohydrates. Pancreatic enzymes move from the pancreas to the intestine through the pancreatic duct 28 which, in most individuals, combines with the bile duct 32 from the gall bladder 26 to form a common duct that enters the intestine through the Ampula of Vater 30 (also called the Ampulla of Vater, hepatopancreatic ampulla, ampulla biliaropancreatica). However, in some individuals, the bile duct 32 and pancreatic duct 28 remain separate and enter the small intestine 20 at separate location.

As the food fluid journeys through the small intestine 20, digested foodstuff, such as Pats, are absorbed through the mucosal cells into both the capillary blood and the lacteal 38. Other digested foodstuffs, such as amino acids, simple sugars, water, and ions are absorbed by the hepatic portal vein 40. From the small intestine 20, the remainder of the food fluid enters the large intestine 42 whose major function is to dry out indigestible food residues and eliminate them from the body as feces 44 through the anal canal 46.

Current gastrointestinal tract surgeries require incisions to be made into the abdomen in order to attach the distal small intestine to the stomach and to make the stomach smaller. This procedure is sometimes called "Roux-en-Y" or gastro-jejunal bypass with gastric reduction. The procedure is commonly performed through a large midline abdominal incision, although some surgeons have developed adequate skill to perform the procedure through a number of smaller incisions in a laparoscopic manner with cameras and instruments inserted through the holes for visualization. Both methods cause weight loss through bypass by reducing the effective length of intestine available for the absorption of food and the stomach is reduced in size so that the patient cannot eat a lot of food. However, both methods require anesthesia (usually general), a prolonged recovery time, and are not reversible once the target weight of the patient is reached.

Another procedure used is vertical stapled gastroplasty. This procedure involves incision of the anterior abdominal wall and creation of a 10-15 ml pouch from the proximal stomach by use of 4-6 rows of staples, with hundreds of staples in each row. This procedure also has numerous complications including rupture of the staple line, infection of the surgical incision, post operative hernias and the like. Moreover, due to the large amount of fat tissue in the anterior abdominal wall in the typical patient on whom this procedure is performed, poor healing of the operative wound ma result. Furthermore prolonged post-operative bed rest after such extensive surgery predisposes obese patients to the development of deep vein thrombosis and possible pulmonary emboli, some with a potentially lethal outcome.

BRIEF SUMMARY OF THE INVENTION

Devices and methods are described for modifying the location at which bodily fluids interact with nutrients in a gastrointestinal tract using an implant having a conduit and fasteners to divert bodily fluids from an entrance within a gastrointestinal tract to a location downstream from the entrance.

In certain embodiments, methods and devices for diverting fluid from a single or multiple ducts in a wall of a small intestine by inserting a support frame into the small intestines, the support frame having an opening in a wall and having an elongate conduit member coupled to the support frame, are provided. The elongate conduit generally includes a near portion and a far portion and a lumen extending there between, where the lumen is in fluid communication with the side opening of the support frame at a location between the near and far portions causing the near portion and far portion of the conduit span across the side opening, in the support frame such that the near portion remains proximal to the side opening, the elongate conduit further having at least one distal opening in the far portion. The side opening, of the device is aligned with the duct such that fluid from the duct enters the elongate conduit lumen.

In certain embodiments, devices may include a support frame having a wall defining a passageway, where the wall includes at least one opening, an elongate conduit having a near portion and a far portion and body extending there between, a lumen extending there between, where the lumen is in fluid communication with the side opening of the support frame at a location between the near and far portions causing the near portion and far portion of the conduit to span across the side opening in the support frame such that the near portion remains proximal to the side opening, and at least one distal opening in the tar portion of the elongate member.

Additional variations include one or more kits for bypassing intestinal fluids from the digestive tract comprising a scope-type device and an intestinal implant in accordance with those variations described herein.

In certain embodiments, an intestinal implant for preventing the interaction of fluid with a portion of the small intestines comprising a body means for diverting fluid from the opening, in the intestines, a passage means or conduit for conveying fluid to a distal location in the intestines, and a securing means for securing the implant to a wall of the intestines is provided. The securing means may comprise the fasteners discussed herein or may comprise other methods of securing the implant to the intestinal wall as also discussed herein.

In certain embodiments, a device for diverting fluid from a duct in a wall of the GI tract, e.g., a wall of a small intestine, is provided. The device may include a support frame having a first cuff, a second cuff, a central portion and a passageway extending through the central portion and/or between the first and second cuffs. The central portion may have a reduced diameter relative to a diameter of the first and/or second cuffs and at least one opening in a side-wall of the central portion. The first and second cuffs may be expandable with the second cuff being configured to form a fluid tight seal against the wall of the small intestine at a location distal to a duct opening and the first cuff being configured to form a fluid tight seal against the wall of the small intestine at a location proximal to the duct opening. The first and second cuffs in combination with an exterior wall of the central portion and a wall of the small intestine define a reservoir for receiving fluid from the duct.

A conduit may be coupled to the side-wall of the central portion of the support frame. At least a portion of the conduit extends within the passageway and the conduit may have a first end, a second end, a side-wall having an opening, and a lumen. The opening in the side-wall of the conduit may be coupled, connected or secured to the opening in the side-wall of the central portion such that fluid entering the opening in the side-wall of the central portion from the reservoir or directly from the duct passes through the opening in the side-wall of the conduit and into the conduit lumen. A diameter of the conduit may be smaller than a diameter of the passageway such that foods and other digestive substances may pass through the passageway and past the conduit without entering the conduit or entering the conduit in a reduced manner.

In certain embodiments, a method for diverting fluid from a duct in a wall of the small intestine is provided. The method may include inserting a device into the small intestine. The device includes a support frame having a first cuff, a second cuff, a central portion and a passageway extending between the first and second cuffs and/or through the central portion. The central portion may have a reduced diameter relative to a diameter of the first and/or second cuffs and at least one opening in a side-wall of the central portion. A conduit may be coupled to the side-wall of the central portion where at least a portion of the conduit extends within the passageway and a diameter of the conduit is smaller than a diameter of the passageway. The conduit may have a first end, a second end, a side-wall having an opening, and a lumen. An opening in the side-wall of the conduit ma be coupled, connected or secured to the opening in the side-wall of the central portion such that fluid entering the opening in the side-wall of the central portion passes through the opening in the side-wall of the conduit and into the conduit lumen.

The device may be positioned within the small intestine such that the second cuff is located distal to a duct opening and the first cuff is located proximal to the duct opening. The first and second cuffs may be expanded or fit against the wall of the small intestine such that the second cuff forms a fluid tight seal against the all of the small intestine distal to the duct opening and the first cuff forms a fluid tight seal against the wall of the small intestine proximal to the duct opening. The first and second cuffs in combination with an exterior wall of the central portion and a wall of the small intestine define a reservoir for receiving fluid from the duct. Fluid can be diverted or rerouted from the reservoir or directly from the duct opening through the opening in the side-wall of the central portion and into the opening in the side-wall of the conduit. The fluid passes from the opening in the side-wall of the conduit, through the conduit lumen and drains from the second end of the conduit positioned within the GI tract or small intestine at a distance from the opening in the side-wall of the conduit, the opening in the central portion, and/or the first end of the conduit. During use, food and other digestive substances may pass through the passageway and past the conduit without entering the conduit or where substances enter the conduit in a reduced manner.

Although not required, the devices described herein may be implanted in a minimally invasive manner using a scope directed through a natural body opening (such as a gastrointestinal opening). It should be noted that any discussions of a scope or endoscope are intended to include the endoscope, colonoscope, duodenoscope, and any other scope type device that is functionally able to implant the device.

It is noted that the subject application generally discusses transporting digestive fluids from a single duct within the small intestines. It is within the scope of the disclosure to employ implants having one or more openings to convey digestive fluids in the event that more than one duct delivers digestive fluids to the small intestines.

This application is also related to commonly assigned U.S. patent application Ser. Nos. 10/687,954; 10/778,365; and 10/799,512, the entirety of each of which is incorporated by reference. Also, U.S. patent application Ser. Nos. 10/910,550 and 11/546,458 are incorporated herein by reference in their entirety.

Variations of the devices and procedures described herein include combinations of features of the various embodiments or combination of the embodiments themselves wherever possible.

BRIEF DESCRIPTION OF THE DRAWINGS

The accompanying drawings, which are incorporated into and constitute a part of this specification, illustrate one or more embodiments and, together with the detailed description, serve to explain the principles and implementations of the invention.

FIGS. 6A and 6B illustrate perspective and side views of a variation of a gastrointestinal device including an outer sheath.

DETAILED DESCRIPTION OF VARIOUS EMBODIMENTS

Various embodiments are described herein in the context of a minimally invasive gastrointestinal bypass. Those of ordinary skill in the art will realize that the following detailed description is illustrative only and is not intended to be in any way limiting. Other embodiments will readily suggest themselves to such skilled persons having the benefit of this disclosure. Reference will now be made in detail to implementations and embodiments as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Where the context permits, singular or plural terms may also include the plural or singular term, respectively. Moreover, unless the word or is expressly limited to mean only a single item exclusive front the other items in a list of two or more items, then the use of "or" in such a list is to be interpreted as including (a) any single item in the list, (b) all of the items in the list, or (c) any combination of items in the list.

Figure 1A:
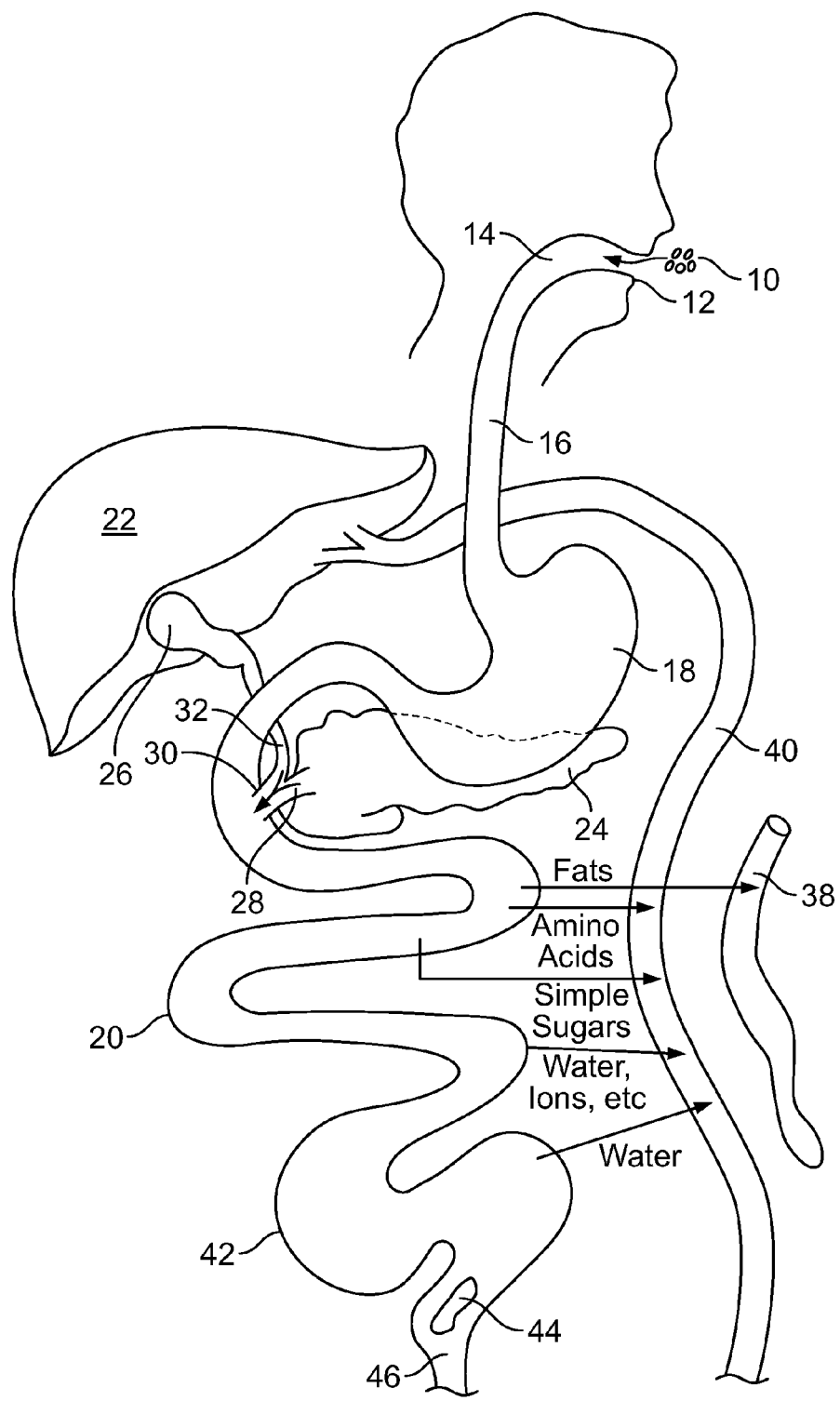
FIG. 1A is an illustration of the digestive system.
Figure 1B:
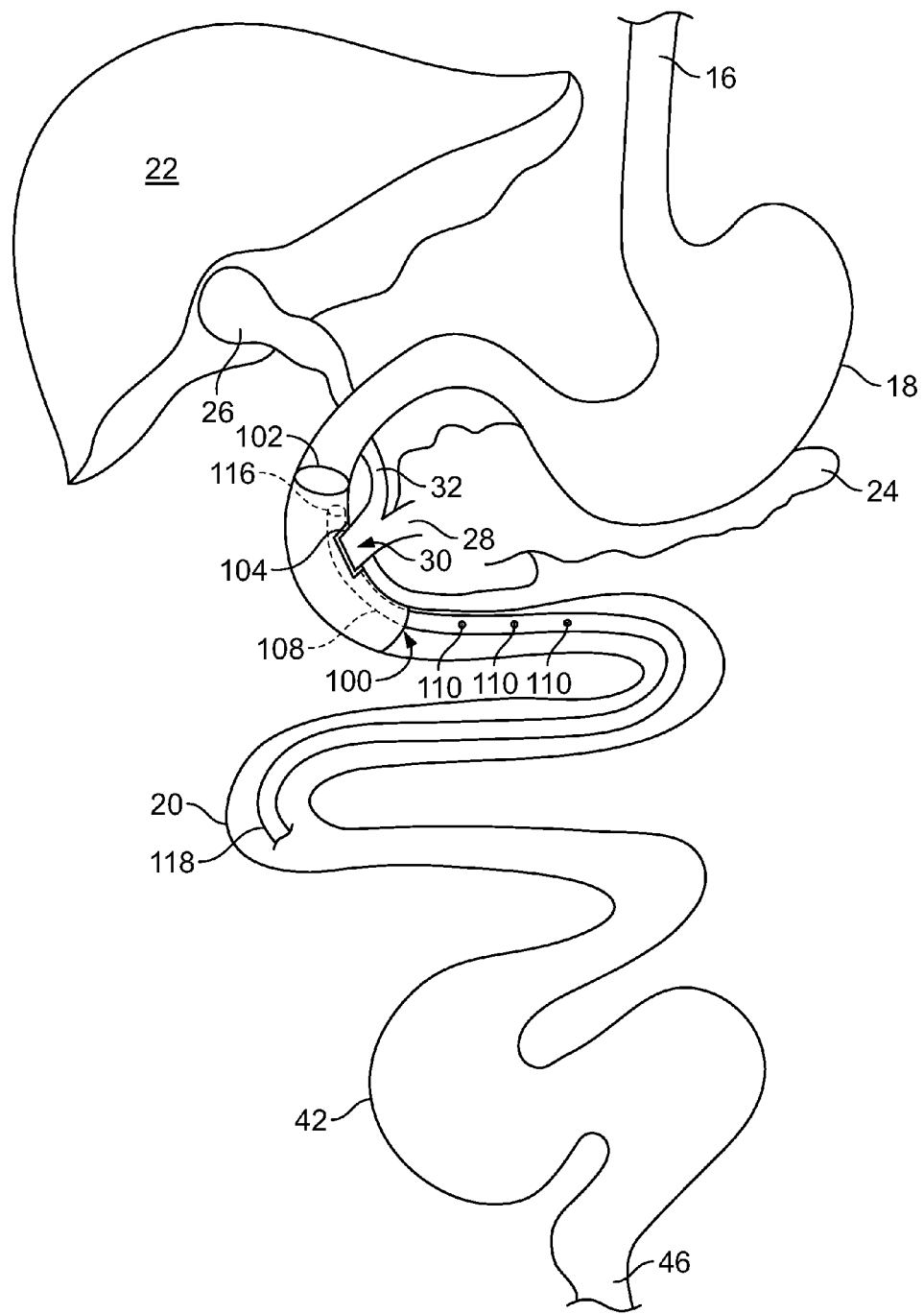
FIG. 1B is an illustration depicting a variation of gastrointestinal device when placed in the small intestines.

In certain embodiments, a system, method, device, and apparatus to treat obesity and other conditions through gastrointestinal bypass is provided. By bypassing bodily fluids such as enzymatic, food, and other fluids to a location distal the tract, less food will be absorbed by the body and more food will be excreted, which results in weight loss. FIG. 1B illustrates a variation of an embodiment of an implant 100. As illustrated the implant diverts fluid from the duct 30 in the wall of the intestines. The implant 100 includes a support frame 102 that secures the implant within the intestines and a conduit 108 that diverts fluid from the duct 30. The support frame 102 can be selected, from various structures such as tubes, stents, basket-type members, or other such structures or combination of structures that prevent migration of the implant 100 within the body.

The support frame 102 will include an opening 104 in a wall or side of the frame 102. The opening. 104 will preferably be placed over the duct 30 to allow fluids to enter the conduit 108 and pass there through. It should be noted that the support frame 102 may be coated or have a tube placed there through to prevent fluids from passing through the wall of the support frame at any location other than the opening 104. Alternatively, the support frame 102 or portions thereof may be constructed to have a mesh or porous structure. Such a structure may aid in securing the implant within the intestinal wall. Furthermore, the implants described herein may have an antibacterial coating either on the support frame, on the barrier 120, on the elongate member 108, or in a combination of locations. The antibacterial coating may be used to prevent colonization of bacteria within the implant.

The support frame 102 may include anchors, ribs, protrusions, or other components (not illustrated) to aid in securing of the device (For example, see US Published Patent Applications 2004/0107004A1 and 20041249362A1, the entirety of each of which is incorporated by reference. Such components may be solely located on the support frame 102. Alternatively, these components may also be located on the elongate member 108, either alone or in combination with fasteners on the support frame. Additional variations include an implant 100 which relies upon an adhesive to secure a portion or all of the implant 100 to the tissue wall. The adhesive or sealant may be any type that is used in medical procedures and may be used alone or in combination with the fastening components.

FIG. 1B also illustrates the elongate conduit as having a near portion 116 and a far portion 118. As discussed in more detail below, the near portion 116 may serve as a reservoir for fluids that would otherwise be blocked by food substances within the tract of the intestines. Accordingly, the near and far portions 116, 118 shall span across the opening 104 so that when food or other substances block the conduit in the far end for distal to the opening), fluids exiting from the duct 30 may pass into the near end 116 of the elongate member 108 and subsequently pass from the implant 100 after clearing of the obstruction. Therefore, the near end portion 116 may serve as a reservoir for the implant 100. In many variations of the device 100, the near end 116 will be constructed to remain proximal to the opening 104.

The elongate conduit 108 illustrated in FIG. 1B can also include a number of openings or apertures 110 in the conduit body. Although the apertures 110 are optional, they may assist in preventing fluid from accumulating in the conduit 108 due to obstruction or constriction of the conduit 108. In some embodiments, the implant 100 may comprise an absorbable substance placed over the apertures 110 so that fluid only exits the apertures 110 if there is a back flow due to fluid build-up in the conduit 108. Alternatively, the apertures 110 may include valves that prevent food substances from entering the conduit 108 but allow fluid to exit due to a building of pressure in the conduit 108.

In some embodiments, the implant 100 may include a conduit 108 comprised of a porous material, or at least having a porous section to prevent accumulation of fluid or pressure. The conduit 108 may be comprised from a non-absorbable material or a bio absorbable material to provide a temporary placement within the intestines. Additional variations of the implant 100 may have multiple conduits 108 of the same or different lengths.

The conduit 108 may have one or more lumens such that blockage of one lumen will not block the entire conduit 108. Accordingly, multiple tubes may be used or one or more multi-lumen tubes may be used.

In some embodiments, it may be desirable to size the lumen of the conduit 108 to be large enough in diameter such that the enzymes may pass through the conduit 108 without forming stones or causing infection. During placement of the implant 100, the conduit 108 may be compressed, folded, or rolled when implanted. To deploy the conduit 108 fluids, such as saline or gas may be inserted into the implant 100, through either the body portion 102 or the conduit 108 to extend, straighten, or unfurl the conduit into the GI tract. Such a feature may also be used to clear a blocked conduit 108 of any obstructions. However, it is also contemplated that the conduit 108 may unfurl itself by having the bile and pancreatic secretions fill the conduit or through intestinal peristalsis. Accordingly, the implant 100 may include a port or valve for allowing delivery of fluids to extend or clear the conduit 108.

The length of the conduit 108 may be selected such that it limits the interaction of digestive fluids as desired. The conduit 108 length at the distal end, away from the body, may be adjustable. The amount of malabsorption as a result of the conduit 108 is related to the length of the bowel pass by the conduit. Thus, the location of where the enzymatic fluids are to exit in the GI tract may be variable and may be determined by the doctor. The conduit 108 may be shortened by trimming its length prior to insertion into a patient's body.

In addition, the elongate member 108 may be sufficiently flexible to allow peristalsis to "milk" the elongate member to assist with moving the fluids there through. In additional embodiments, the elongate member 108 may be fabricated such that the interior walls of the member temporarily adhere together. This feature allows the elongate member 108 to serve as a fluid barrier and prevent reverse flow of substances within the implant.

Figure 2A:
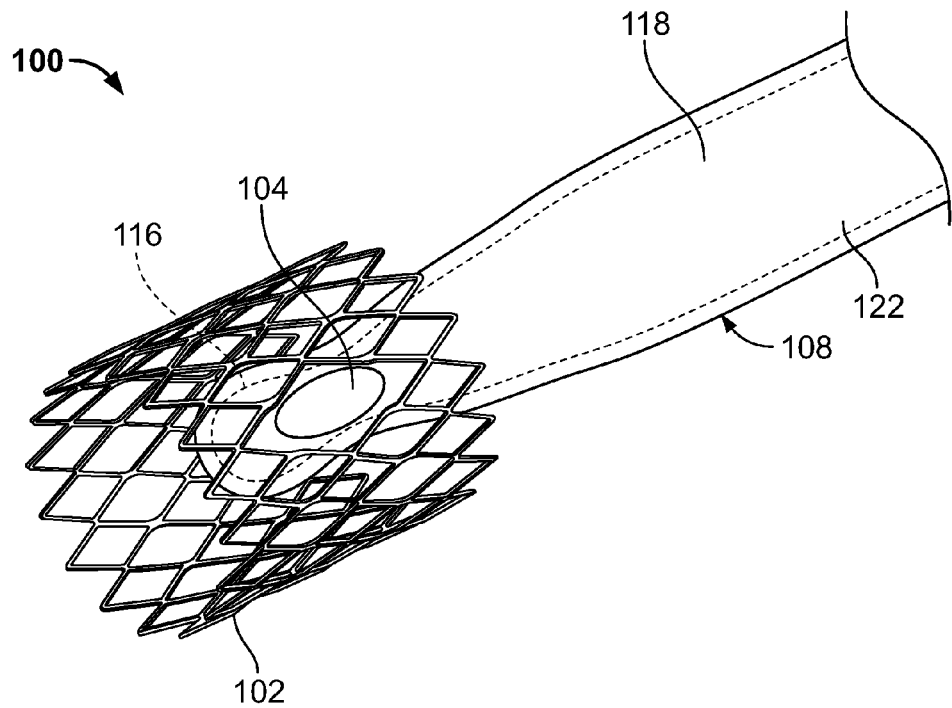
FIGS. 2A-2G represent variations of a gastrointestinal device.

FIGS. 2A-2D illustrate variations of implants 100. As shown in FIG. 2A, the implant includes a support frame 102 having an opening 104 in a side or wall. The opening is sized to allow for fluids to enter from, for example, the Ampula of Vater and pass into the conduit 108. As noted herein, the support frame may be a stent-type structure, a tube, or any similar structure that secures the implant within the small intestines and at the desired site. The support frame 102 may be constructed from a metal, alloy, shape-memory alloy, polymer, etc. The support frame 102 may be plastically deformable (such that a balloon or other mechanical expansion) deforms the frame 102 into place. Alternatively, it may be elastic such that it is restrained to conform to a small delivery profile and upon deployment is unrestrained to expand into place. In yet another variation, the support frame 102 may be a shape memory alloy and expand into shape upon reaching a particular temperature. In either case, it is important to note that certain embodiments include support frames 102 that are sufficiently elastic when implanted so that the support frame 102 expands within the bowel to permit passage of a food bolus without becoming dislodged. In this manner, the degree of expansion of the support frame 102 would be similar to that of the normal bowel.

Figure 2B:
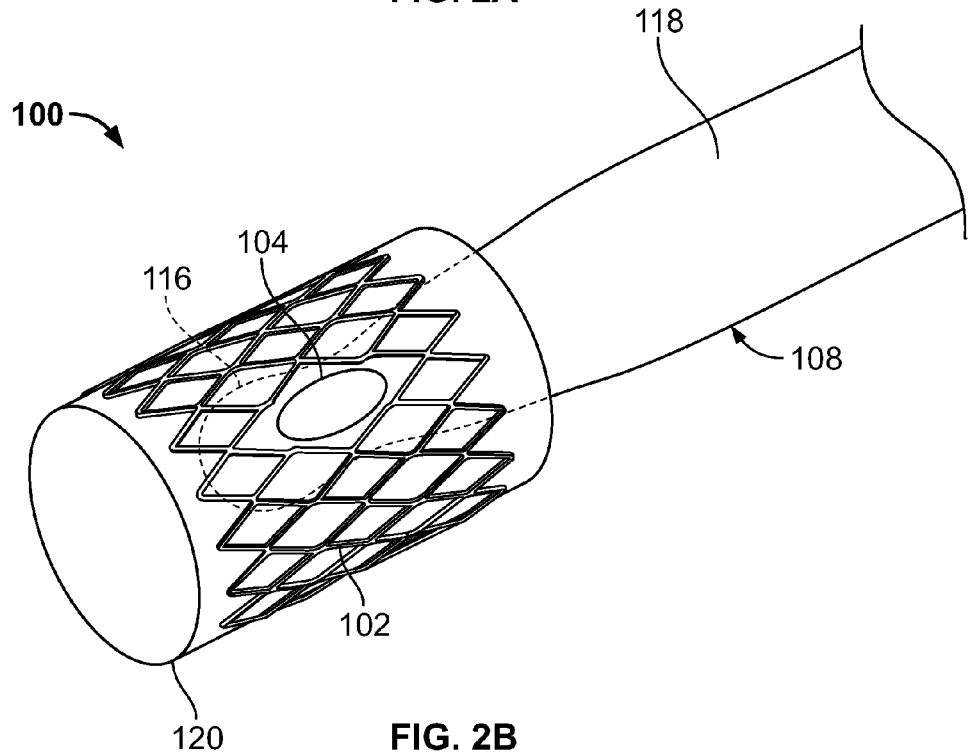

FIG. 2B illustrates another variation of an implant 100 where the support frame 102 includes a barrier 120. The barrier 120 may assist in directing fluids to the opening 104 or may provide a smooth internal surface for the support frame 102 to prevent food particles from becoming lodged within the frame 102. The barrier 120 may be formed from a polymer coating or may be the same material as the elongate member 108. For example, the barrier may comprise a polymer selected such as a thermoplastic polymer, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

The implant 100 further includes an elongate member 108 that is attached or otherwise coupled to the support frame 102 to allow fluids that enter the opening 104 to pass directly into a lumen of the conduit 108. The elongate member further includes a near portion 116 and a far portion 118 that span across the opening 104 to allow the near portion 116 to function as a reservoir.

Figure 2C:
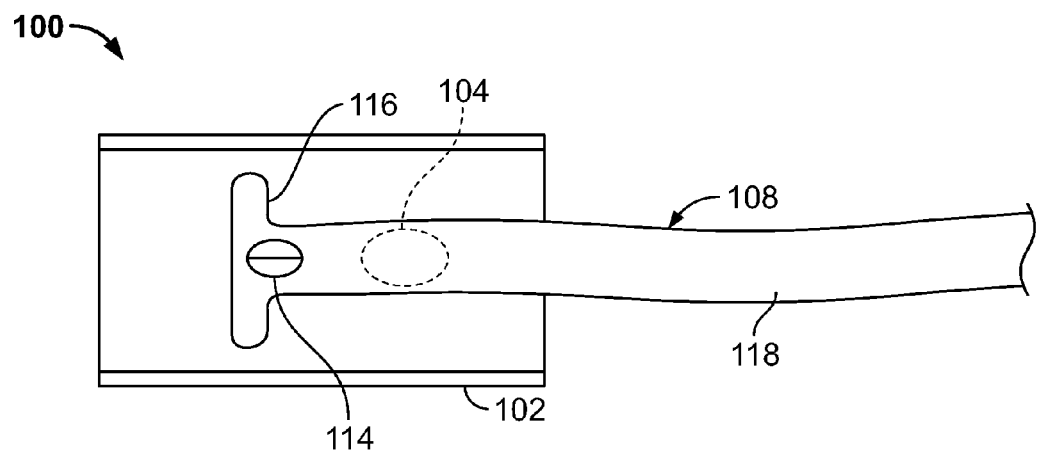

FIG. 2C illustrates a cross-sectional view of an implant 100. In this variation, the elongate member may include a valve 114 that allows for insertion of fluids to assist in deploying the far side 118 of the elongate member 108 or to remove blockages from the member 108. Such irrigation and/or inflation tubes used to assist in deploying or clearing, the member may extend outside of the mouth or body in those cases where frequent irrigation is required. In this variation, the near portion 116 of the elongate member 108 comprises a "T" shape. It should be understood that any shape that allows for the near portion 116 to function as a reservoir is contemplated.

Figure 2D:
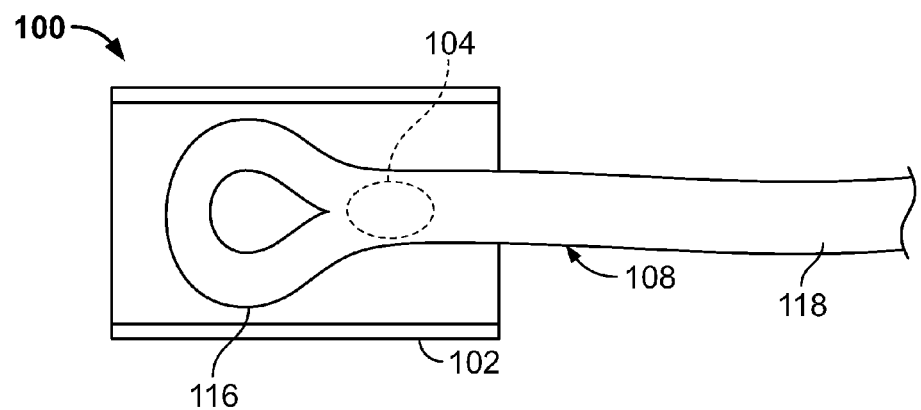

FIG. 2D illustrates a cross-sectional view of another variation of an implant 100. In this variation, the near portion 116 comprises a loop shape. Though not shown, the near portion 116 can be secured to the support frame 102 such that it remains in the near or proximal section of the frame 102.

The near portions 116 described herein may be fabricated, with a profile that minimizes interference with substances passed from the stomach through the intestines. In one variation, the near portions 116 may have a low profile so as not to create a point of obstruction at the proximal end of the implant that accumulates food and other particles within the small intestines. Moreover, the near portion 116 may be fabricated to have a thinner wall thickness than the remainder of the conduit 108.

Figure 2E:
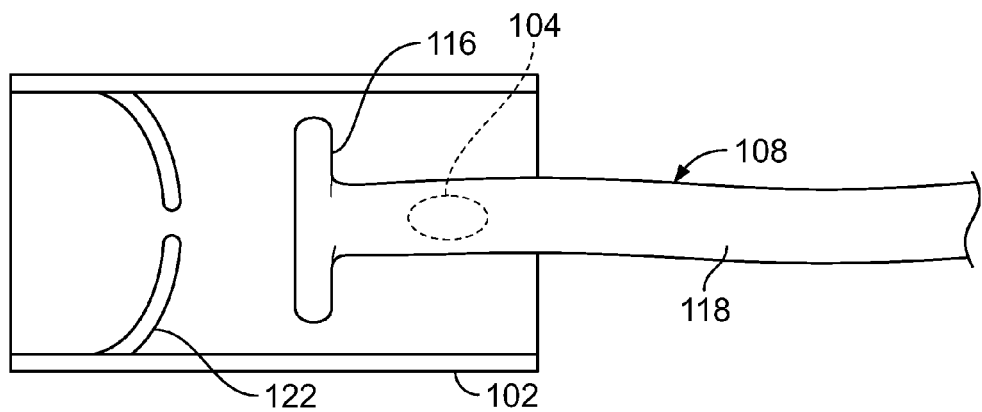
Figure 2F:
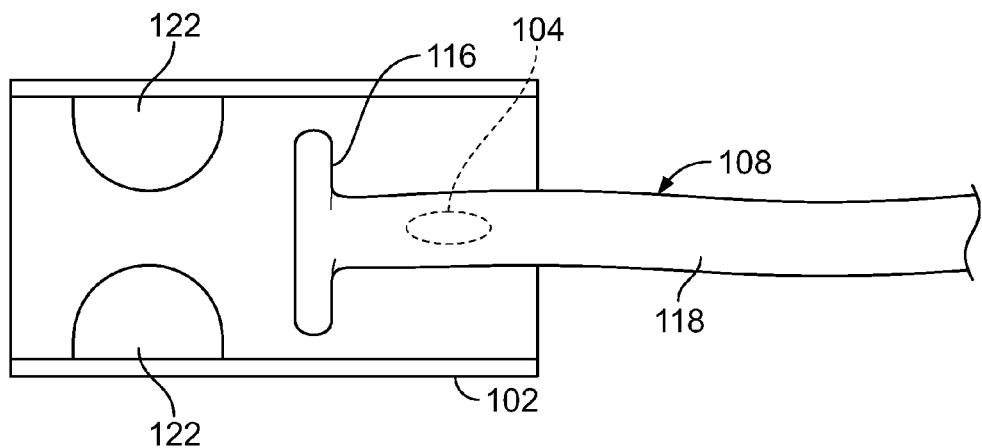

The implant 100 may further include a restricting, portion 122. The restricting portion 122 may be used to reduce the rate of gastric emptying. The restricting portion 122 illustrated in FIG. 2E may be one or more baffles, valves, funnels, etc. that reduce the size in a portion of the implant 100. The restricting portion 122 may be a part of the support frame or inserted into the support frame after deployment into the bowels. Alternatively, as shown in FIG. 2F, the restricting portion 122 may comprise one or more inflatable members such as a bladder or balloon. Accordingly, the restricting portion 122 may be inflated to a desired size after implantation of the support frame 102. The restriction member 122 may be a valve.

Figure 2G:
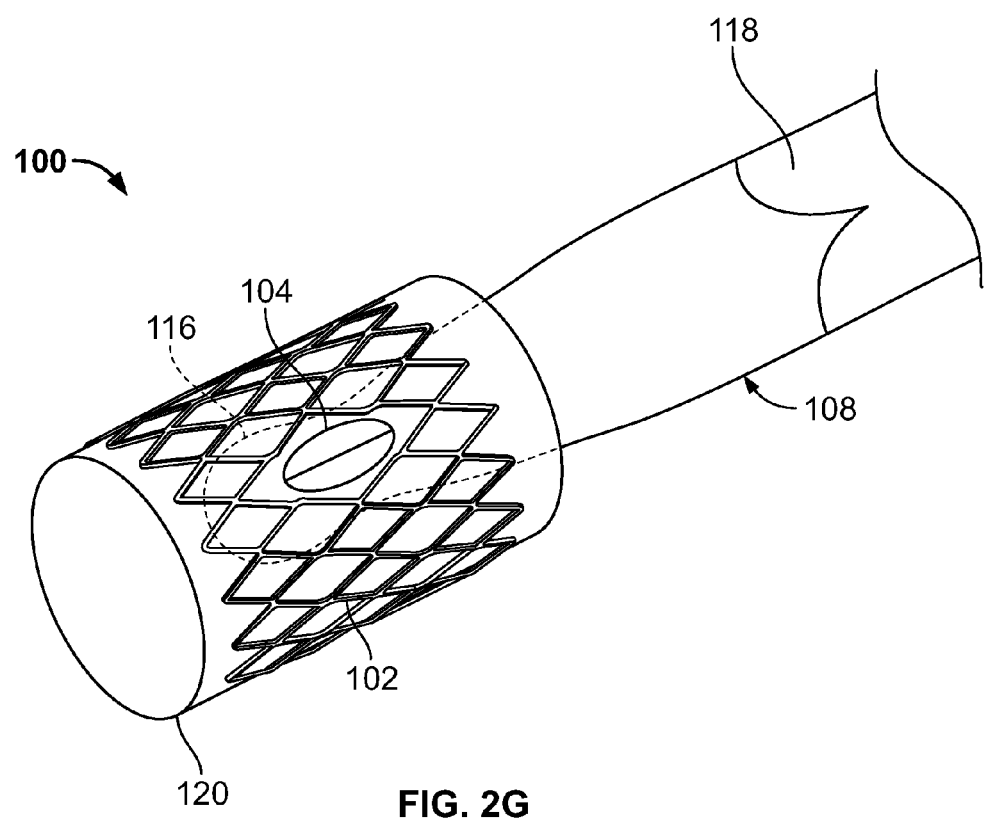

FIG. 2G shows another embodiment. In this variation the aperture 104 and/or the conduit 108 may include a valve. The valve may also be located in one or more apertures 110.

Figure 3A:
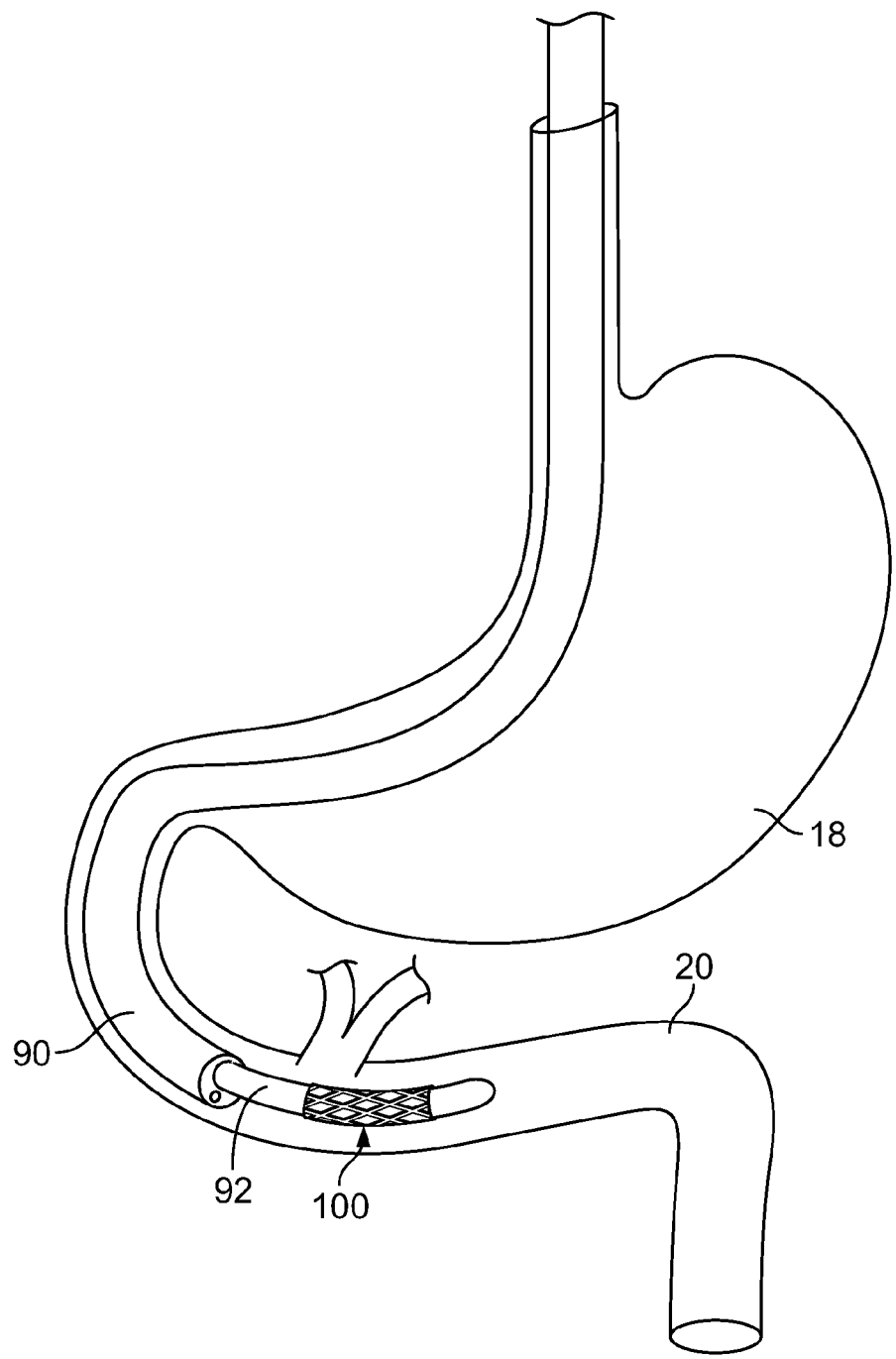
FIGS. 3A-3D represent schematics of a variation of a gastrointestinal device when placed and during passage of food-substances within the small intestines.

FIG. 3A illustrates advancement of an implant 100 to a site within the small intestines 20. As shown, the implant 100 may be mounted on a delivery catheter 92. Use of a scope 90 is optional but preferred. The implant 100, catheter 92, and/or scope 90 may have a mark or other indicator to aid the operator in aligning the opening (not shown) with the Ampula of Vater 30. Preferably, during deployment, the far end of the elongate member (not shown) is folded or otherwise placed within the implant 100 or delivery catheter 92.

Figure 3B:
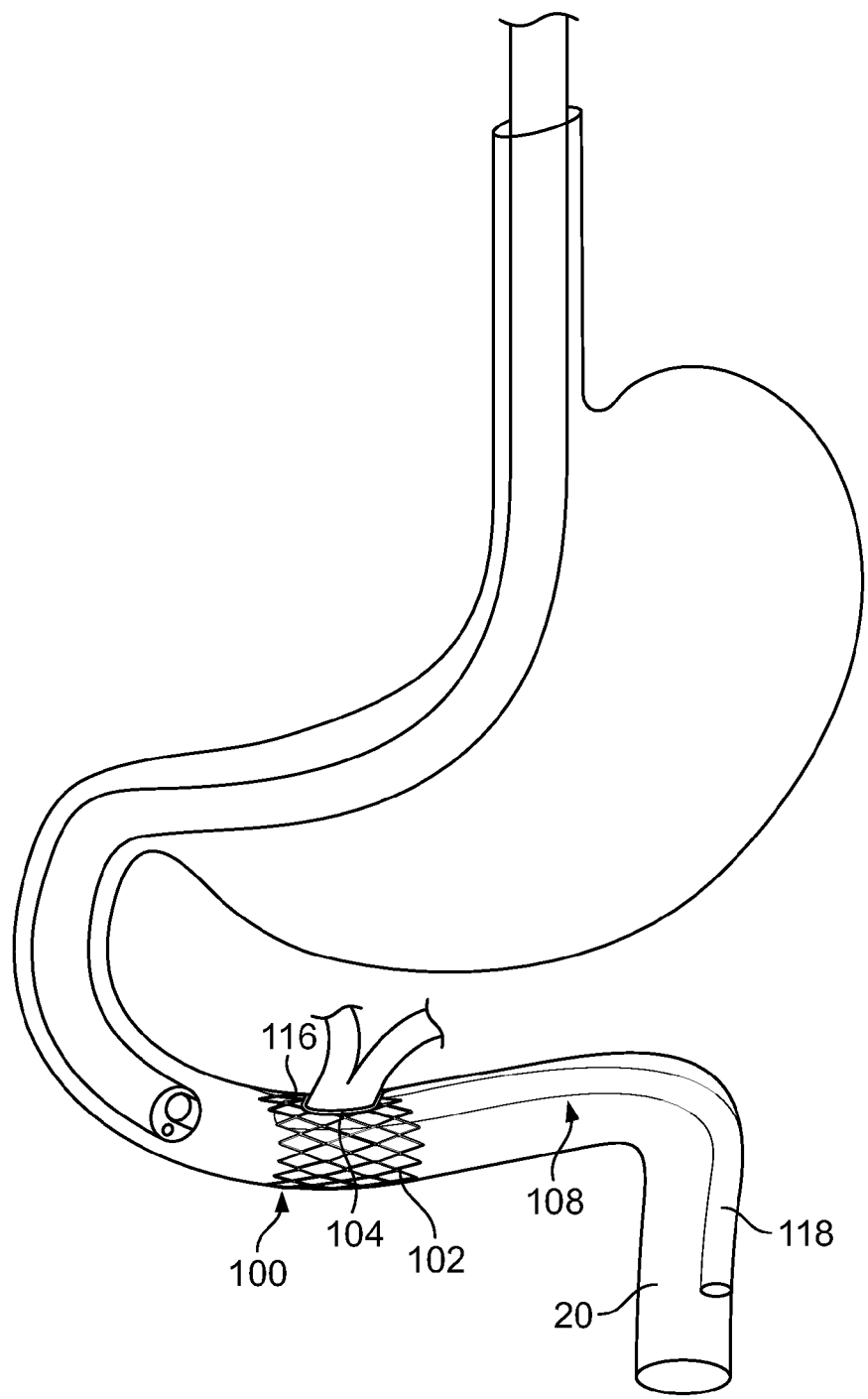

FIG. 3B illustrates the implant 100 after placement within the small intestines 20. Although not shown, the implant 100 may be placed with the use of a balloon or other expansion means. Alternatively, the implant may self-expand to fit within the small intestines 20. Fluid may be used to deploy the far end 118 of the elongate member 108 distally in the small intestines 20. However, the elongate member 108 may self-deploy over time. As shown, the near portion 116 of the implant 100 is located proximal to the opening 104. The far portion 118 of the elongate member 108 is placed distally in the intestines so that the near and far portions 116 and 118 span across the opening 104.

Figure 3C:
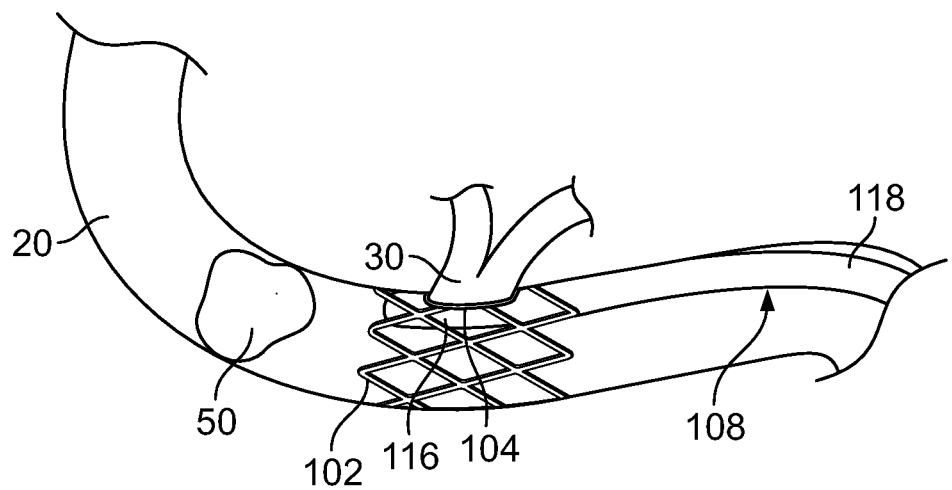
Figure 3D:
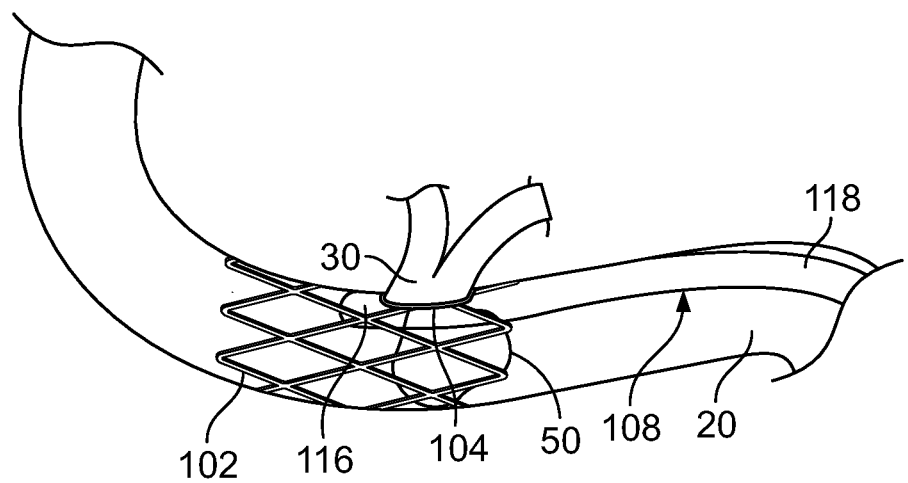

FIG. 3C is a schematic that illustrates a principle of the functionality of the devices described herein. As shown, a bolus 50 of food travels through the small intestines. As shown in FIG. 3D, as the bolus 50 passes adjacent to or distal to the Ampula of Vater, the bolus 50 blocks the conduit 108. However, the digestive fluids continue to enter the conduit 108 via the opening 104. Thus, the near section 116 of the elongate member 108 serves as a reservoir and captures the digestive fluids that would otherwise be blocked due to the bolus 50. It should be noted that as subsequent food particles pass through the small intestines, the digestive fluids located in the near portion 116 are forced towards the far end 118 of the conduit 108. Typically, the Ampula of Vater 30 has a valve that prevents the digestive fluid from passing back into the duct.

Various means may be employed to restrain the support frame 102 and/or elongate member 108 within the intestines. Such means may include wire or polymeric strands, sleeve-like devices, or woven mesh structures to tie the support frame 102.

The polymers for use in various embodiments may include polymers such as thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof. Moreover, variations include an implant where the body portion comprises a bioabsorbable polymer.

As described herein, the device 100 shortens the effective absorption length of the bowel or GI tract. The effective absorption is the amount of digested food that is absorbed by the body. By bypassing the bodily fluids in the GI tract, such as bile and pancreatic enzymes, to a location further downstream within the GI tract, nutrients from the food fluid will not be absorbed by the enzymes or emulsifying reagents in the body as it travels from the stomach and through the intestine. This will also reduce the time available for absorption of the food fluids into the body. Thus, the effective absorption of nutrients from the food fluids is decreased whereby most of the food fluids are excreted which results in the patient's weight loss.

The conduit 108 may be a flexible tube having a first end configured to divert enzymatic and/or emulsifying fluids to a location significantly further down the GI tract. In certain embodiments, the end of the conduit is closed and acts as a reservoir for fluid entering from the side opening. The conduit 108 may be large enough in diameter such that the enzymes may pass through the flexible tube without forming stones or becoming infected. In an alternative embodiment, the conduit may contain a plurality of apertures 110 to allow some enzymatic fluids to pass through to prevent injury or death to the patient should the conduit become clogged. The conduit 10S may also have a side port (not shown) to allow fluids, such as saline, or gas to pass through the conduit to extend, straighten, or unfurl the conduit into the GI tract as will be further described below. This may also ensure that the lumen of the conduit is free and clear of any obstructions. However, the conduit may unfurl itself by having the bile and pancreatic secretions fill the conduit or through intestinal peristalsis.

The length of the conduit 108 at the far portion 118 may be adjustable depending on the needs of the patient. Since the amount of malabsorption as a result of the implant 100 relates to the length of the bowel by-pass (i.e., the length of the conduit 108), having the ability to adjust the length of the conduit 108 may be desirable. In other words, the location to where the enzymatic fluids are bypassed in the GI tract may be variable and may be determined by the doctor. Additionally, the conduit 100 may be comprised of a structure that adjusts in length after implantation (e.g., a filamentous member may be attached to the conduit such that when the filamentous member is pulled, the conduit 108 shortens accordion style or by inverting the distal end into the more proximal tube like intussusception.)

By modifying the location at which enzymatic fluids interact with nutrients from food fluids in the GI tract the body absorbs less nutrients from food fluids. As a result, the effectiveness of enzyme and emulsifying reagent reacting with the food fluids decreases, and more of the food fluids are excreted. The end effect results in weight loss by the patient having the implant. The implant changes the proportion of absorbed food fluids to excreted food fluids causing the weight loss. Additionally, as is apparent, the patient may continue to consume the same amount of food, but use of the device allows for weight loss.

Figure 4:
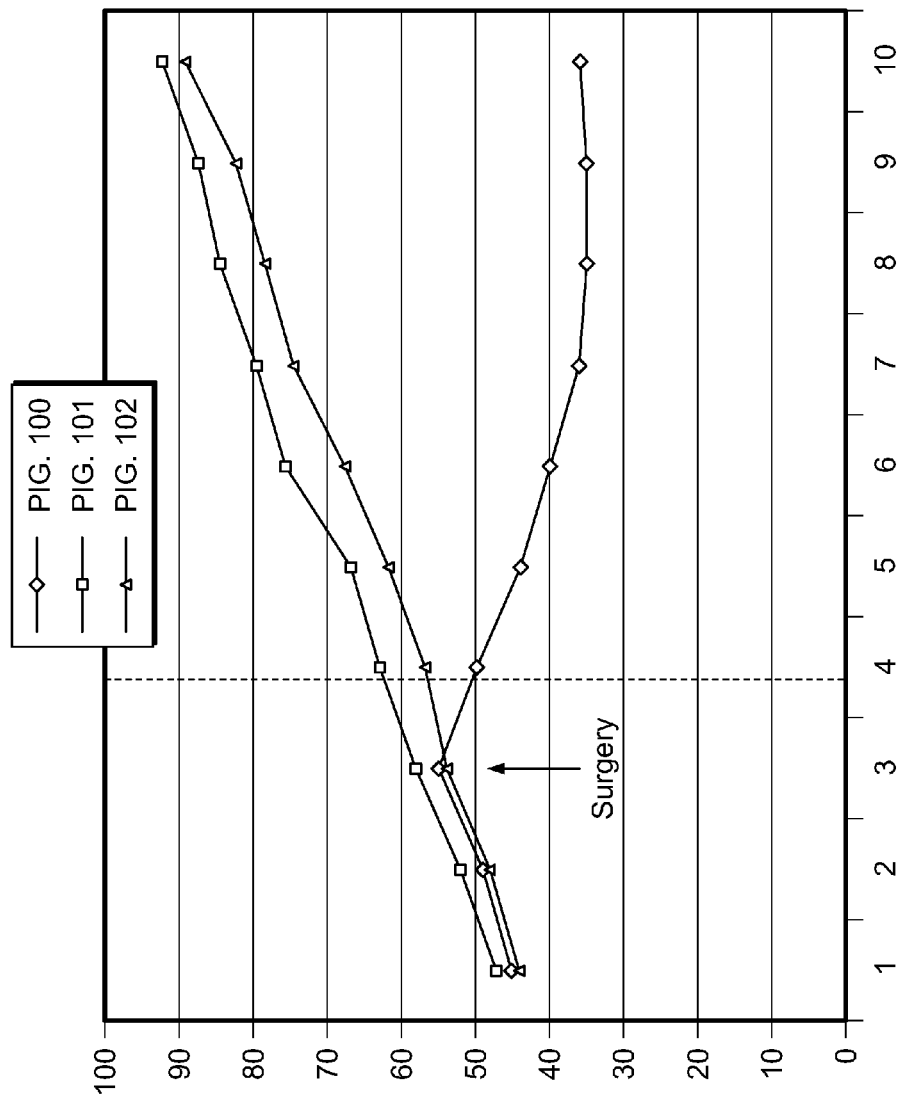
FIG. 4 is a graph illustrating data obtained from testing of a similar device in an animal model.

FIG. 4 is a graph illustrating data obtained from testing the device in a pig animal model. The Y-axis is weight in Kilograms and the X-axis is time in weeks. Pigs A, B, and C consumed food ad libidum throughout the testing period. Pigs B and C were controls (the device was not implanted in these animals). In the experiment, Pig A was implanted with a variation of the implant at week 3. At this time all pigs weighed between 54-59 kilograms. After implantation of the device, Pig A rapidly lost weight in weeks 3 through 7 going from 55 kilograms to 36 kilograms while pigs B and C continued to gain weight. Data after week 7 indicates that Pig A maintained a constant weight at about 35 kilograms for several weeks thereafter. Although Pig A continued to consume the same amount of food each day similar to Pigs B and C. A maintained the lost weight.

It is contemplated that the implant 100 may be inserted into a patient without major surgery, incisions, or the use of general anesthesia. Rather, the patient may be sedated when the device is to be delivered through the mouth of a patient. The length of the device may be adjusted, if necessary, based upon the judgment of the physician or other factors such as the desired weight loss, etc. The length of the conduit may be trimmed or cut by any means. The device is then fitted onto an endoscope. The device may be inserted either prior to inserting the endoscope into the patient's mouth or after insertion of the endoscope into the patient's mouth. However, the device may be formed in any shape possible that would allow for the easiest and safest means to place the device into the patient. By way of example only, and not intended to be limiting, the device may be rolled-up onto itself, the device may be folded into a fan shape, or the device may be folded into a zigzag shape before insertion into the patient's body.

An endoscope locates the placement site (e.g., the Ampula of Vater) for the implant. A retractor may be inserted into the Ampula of Vater. The retractor may have an expandable balloon or a fenestrated tube that may be activated with a vacuum suction to suction the tissue around the Ampula into contact with the body portion. However, other methods of retraction are possible such as a corkscrew that may be screwed into the tissue or a multiple-tined piercing device.

As discussed above, the conduit may have a side port to allow fluids, such as saline, or gas to pass through the conduit to extend, straighten, or unfurl the conduit into the GI tract. This ensures that the lumen of the conduit is free and clear of any obstructions. However, the conduit may unfurl itself by having the bile and pancreatic secretions fill the conduit or through intestinal peristalsis.

The device may be easily removed from the patient's body. Alternatively, the device may remain in the patient's body, but the length of the conduit may be adjusted.

Figure 5:
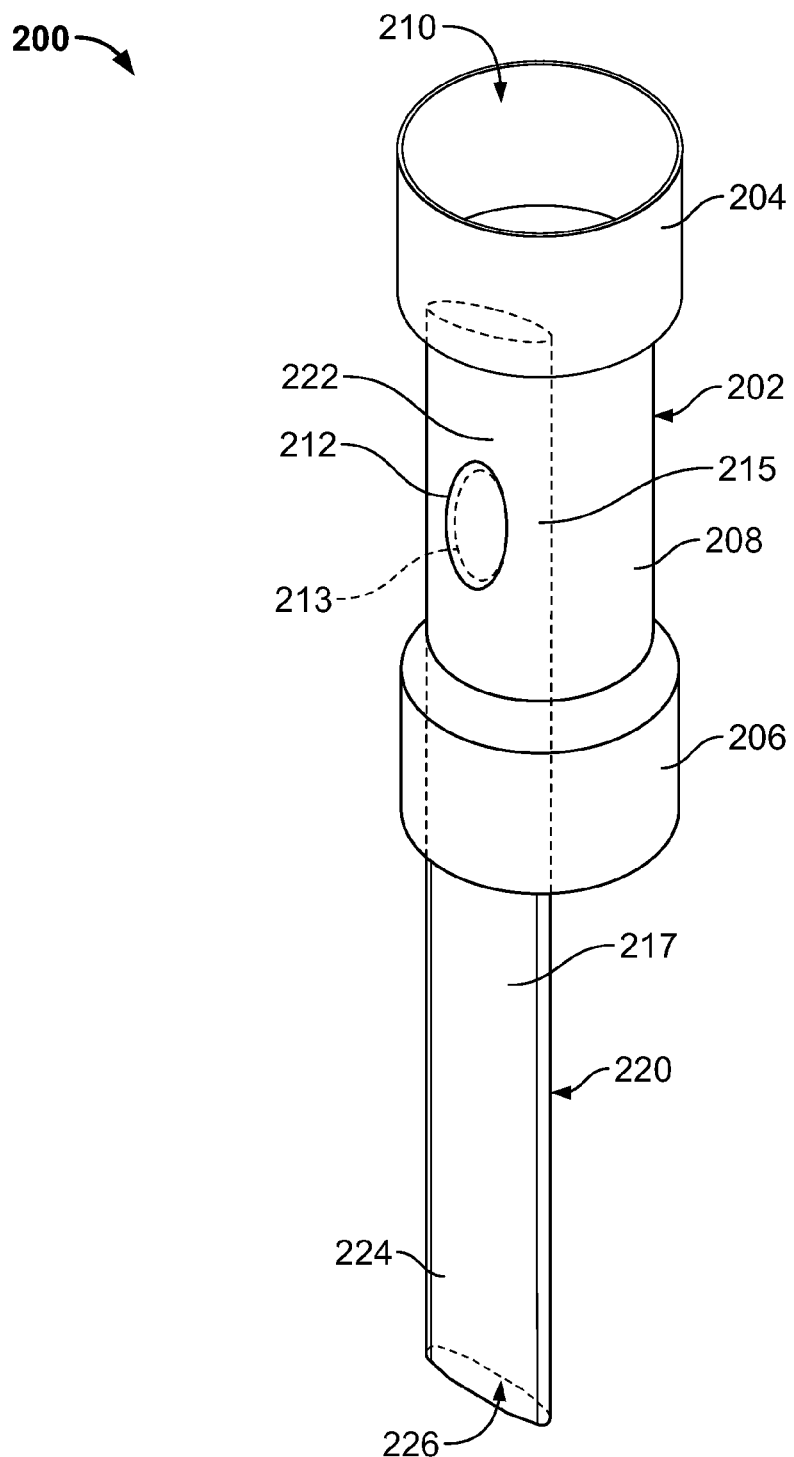
FIG. 5 illustrates a side view of a variation of a gastrointestinal device.

FIG. 5 illustrates an example of a variation of a gastrointestinal device 200 or implant for diverting or bypassing fluids from a duct in a wall of the digestive tract or GI tract, e.g., in the wall of the small intestines, to another area or section of the small intestine or GI tract, e.g., to a location distal the GI tract or distal within the GI tract. The device 200 may include a support frame 202 having a first cuff 204, a second cuff 206 and a central portion 208. A passageway 210 may extend through the central portion 208 and/or between the first and second cuffs 204, 206. The support frame 202 may include openings at both ends in or through the first cuff and second cuff 204, 206 where the openings are in fluid communication with the passageway 210 allowing foods and other digestive substances to pass through the passageway 210. The central portion 208 may have a reduced diameter relative to a diameter of the first cuff 204 and/or the second cuff 206. The central portion 208 also includes one or more openings 212 in a wall of the central portion, e.g., in a side-wall 215 of the central portion. Optionally, in certain embodiments, the opening 212 may be in a side-wall or other wall of the support frame or cuffs of the support frame.

The first and/or second cuffs 204, 206 may be configured or adapted or expanded to contact or to form a seal against a wall of the GI tract. For example, the second cuff 206 may be expanded to form a fluid tight seal or substantially fluid tight seal against a wall of the small intestine at a position or location that is distal to a duct opening. Similarly, the first cuff 204 may be expanded to form a fluid tight seal or substantially fluid tight seal against a wall of the small intestine at a position or location that is proximal to the duct opening. The fluid tight seals formed by the first and/or second cuffs 204, 206, in combination with an exterior wall of the central portion 208 of the support frame 202 and a wall of the small intestine form or define a reservoir 214 (shown in FIG. 9). The reservoir 214 may receive fluid from the duct, thereby allowing fluid to fill or collect in the reservoir 214 and eventually pass from the reservoir through opening 212 in the side-wall of the central portion 208. In certain embodiments, a reservoir is created between the wall of the intestine and the exterior wall of the central portion 208, around the complete circumference of the central portion 208. In other embodiments, the reservoir is created between the wall of the intestine and the exterior wall of the central portion 208, around at least a portion of the circumference of the central portion 208.

Dimensions of the support frame and cuffs may vary. Exemplary dimensions include but are not limited to the support frame having a total length ranging from about 2 cm to about 10 cm or about 4 cm to about 6 cm or having a length of about 5.8 cm. For example, one or more of the cuffs of the support frame may have a length of about 1 cm to about 3 cm or the length of a cuff may be about 1.5 cm long. The central portion may have a length of about 1 cm to about 5 cm or may be about 3 cm long. Optionally, the support frame may taper from the cuffs toward the central portion or toward the center of the support frame. For example, the diameter of one or more of the cuffs may be from about 1 cm to about 5 cm or the diameter may be about 2.7 cm. The diameter of the central portion of the support frame may be from about 1 cm to about 3 cm or the diameter may be about 2 cm.

The support frame may be made from a variety of materials known in the art. Materials used to make the support frame may include but are not limited to silicone and nitinol. Optionally, the support frame may be coated with silicone.

Still referring to FIG. 5, device 200 also includes an elongate conduit 220 coupled to a side-wall 215 of the central portion 20 of the support frame 202. At least a portion of the elongate conduit 220 extends within the passageway 210 of the support frame. The elongate conduit 220 may have a first end 222, a second end 224 having one or more openings, a side-wall 217 having one or more openings 213, and the elongate conduit may have a lumen 226. The opening 213 in the side-wall 217 of the conduit may be, coupled, connected or secured, e.g., in fluid communication, to the opening 212 in the side-wall of the support frame 202 or central portion 208. Indeed, an opening 213 in the side-wall 217 of the conduit 220 may be fastened or secured around opening 212 located in the side-wall 215 of the central portion 208 of the support frame 202. For example, the side-wall of conduit 220 may be connected, coupled, fastened or secured either directly or indirectly to the interior or exterior of the side-wall of the central portion 208 around or near the opening 212. As a result, fluid emptying into opening 212 in the side-wall of the central portion 208 directly from the duct and/or from the reservoir 214 will pass through the opening 213 in the side-wall of the conduit, and the conduit 220 is configured to advance fluid from the opening 213 in the side-wall of the conduit 220 through the lumen 226 to the second end of the conduit 220 where the fluid will empty or drain such that the fluid may be diverted or bypassed via the elongate conduit 220 to another location within the GI tract, e.g., downstream from or distal to the duct.

A diameter of the elongate conduit 220 may be smaller than a diameter of the support frame or the passageway 210 of the support frame 202. The smaller conduit diameter allows foods and other digestive substances to pass through the passageway 210 and past the elongate conduit 220 without entering the elongate conduit 220 or with minimal amounts entering the elongate conduit 220. Optionally, in other embodiments, the opening 212 may be in a wall of a cuff of the support frame or in another portion of the support frame. Optionally, in other embodiments, the conduit and support frame may have openings located in areas or portions other than their side-walls, and such openings may be in fluid communication with one another. In other embodiments, the opening in a sidewall or other portion of the conduit may be coupled to an opening in an end wall or end of the support frame or an opening in an end wall or end of the conduit or other portion of the conduit may be coupled to an opening in a side-wall of the support frame or openings in the end or end walls of the conduit and support frame may be coupled.

When elongate conduit 220 is coupled to the support frame 202, the first end 222 of elongate conduit 220 may be positioned proximal to or upstream from opening 212, within the passageway 210 and/or within the small intestines, while the second end 224 of the elongate conduit 220 may be positioned distal to or downstream from opening 212 within the passageway 210 and/or within the small intestines. In certain embodiments, the second end 224 of the elongate conduit 220 may be positioned within the passageway 210 or within the small intestines at a distance from the opening 213 in the side-wall of the conduit 220 and/or at a distance from the first end 222 of the elongate conduit 220 or the opening 212. The second end 224 may be positioned downstream from and distal to the opening 212 and/or the opening 213 and/or the first end 222. Optionally, the positioning of the proximal end 222 and distal end 224 of the elongate conduit 220 may be interchanged, where the first end 222 is positioned distal to opening 212 and the second end 224 is positioned proximal to opening, 212.

The first end 222 of the elongate conduit 220 may be closed or include an opening. Optionally, the portion of the conduit proximal to the opening 213 or proximal to the opening 212 may be closed. The second end 224 of the elongate conduit 220 may include an opening through which fluid diverted from the duct in the wall of the small intestines and through the lumen of the conduit 220 drains, empties or exits from conduit 220. Optionally, the second cud 224 may be closed or open and/or the conduit 220 may be provided with one or more openings in the side-wall of the conduit located downstream from or distal from the opening 213, which allow for draining of the diverted fluid.

The elongate conduit 220 may be flexible. The elongate conduit may be made from a variety of materials known in the art. Materials used to make the elongate conduit may include but are not limited to various polymers, e.g., thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof. Optionally, the elongate conduit 220 may include a bioabsorbable material. Optionally, the elongate conduit 220 may include silicone. Dimensions of the elongate conduit may vary, including but not limited to the conduit's width, height, length, diameter, etc. Exemplary dimensions of the conduit include but are not limited to the elongate conduit having a diameter or width of about 1 cm to 4 cm or a diameter of about 1.8 cm. The elongate conduit may be about 1 mm to about 5 mm thick or may be about 3 mm thick. The elongate conduit may have a length ranging from about 20 cm to 200 cm or about 100 cm to about 300 cm or the length may be about 150 cm long. The length may be variable or adjustable.

The elongate conduit 220 may be coupled or fastened to the support frame 202 by a variety of mechanisms and in a variety of configurations. For example, the portion of the elongate conduit 220 extending within the passageway 210 of the support frame 202 may be partially or completely bonded or attached to the curvature of the passageway 210 or to the interior wall of the support frame 202.

Figure 7:
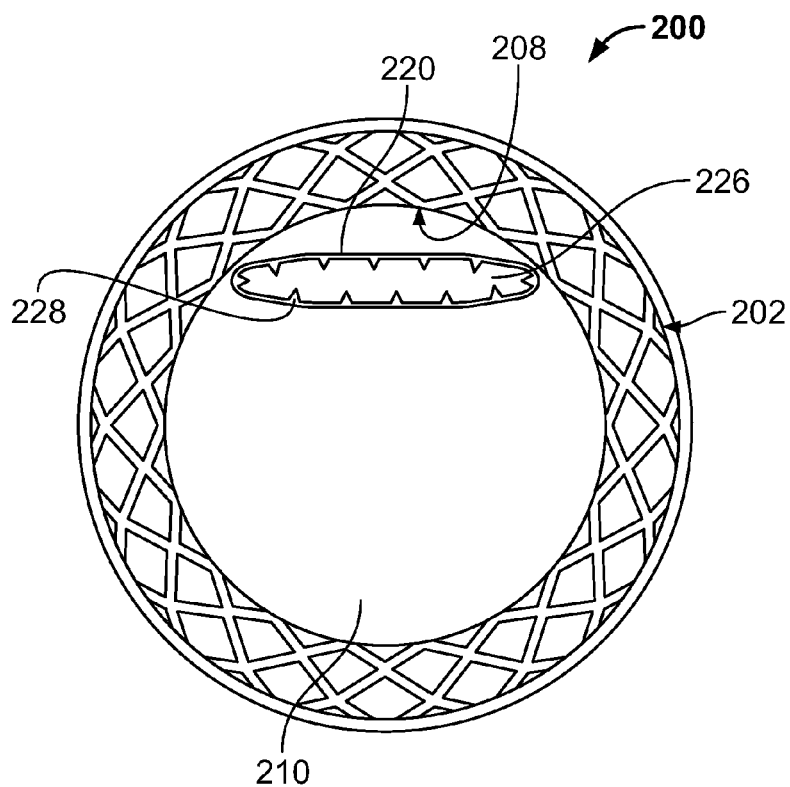
FIG. 7 illustrates at top cross sectional view of a variation of a gastrointestinal device.

Optionally, as shown in FIG. 7, elongate conduit 220 may be coupled to the opening 212 in the side-wall of the central portion 208 support frame 202, and a gap or spacing, may exist between the non-coupled portion of the elongate conduit 220 and the passageway 210 or interior wall of the central portion 208 of the support frame 202. The elongate conduit 220 may also be length and/or width adjustable.

Figure 8:
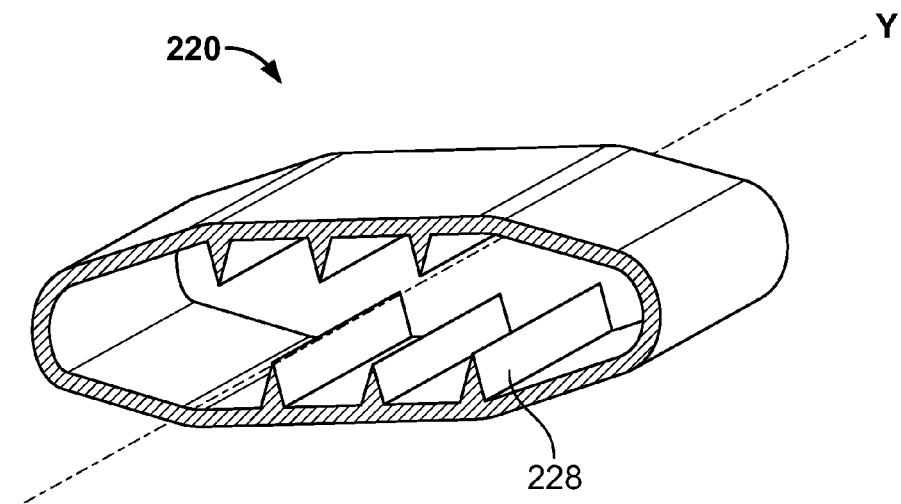
FIG. 8. illustrates a sectional view of a portion of a ribbed elongate conduit of a gastrointestinal device.

As illustrated in FIG. 8, which shows a cross section of a portion of an elongate conduit 220, in certain embodiments, the elongate conduit 220 may include one or more ribs 228 positioned on an interior or luminal wall of the elongate conduit 220. The ribs 228 may extend or protrude substantially toward a central longitudinal axis (axis Y) of the elongate conduit 220 and the ribs 228 may help prevent the elongate conduit 220 from closing on itself or at least prevent complete closure of the conduit 220 on itself or reduce the frequency with which the conduit 220 closes on itself and restricts the flow of diverted fluid through the conduit. In certain embodiments, a plurality of ribs 228 are positioned along a longitudinal length of an interior or luminal wall of the elongate conduit 220 where the ribs 228 extend or protrude toward a central axis of the elongate conduit 220. Dimension of the ribs may vary, including but not limited to rib height, width, shape, the spacing between ribs along the interior or luminal wall of the conduit 220, and the distance of the ribs from the conduit center and ends and the number of ribs. Dimensions may be altered depending on the material used to construct the ribs and the amount of control required or desired over conduit closure. Various dimensions for the ribs or conduit which are suitable to allow the conduit to perform the functions described herein are contemplated. For example, in certain embodiments, a conduit may include ribs having a 50 to 70 degree angle or a 60 degree angle, distance between end ribs on opposing sides of a conduit may be from about 0.2 to 0.4 inches, the distance between adjacent ribs may be from about 0.07 to 0.15 inches, the height of a rib may be from 0.01 to 0.07 inches or 0.02 inches, the diameter of a conduit may be from about 0.5 to 1 inches. In certain embodiments, the conduit may have a width ranging from about 0.03 to about 0.15 inches.

The elongate conduit 220 may be configured such that it allows or encourages fluid to move through the lumen 226 of the elongate conduit 220 in order to drain the reservoir 214 or divert fluid directly from the duct. For example, the dimensions or configurations of the elongate conduit may allow for capillary action or capillary attraction to encourage or move fluid through the lumen 226 of the elongate conduit 220 from the opening 213 in the side-wall of the conduit 220 to the second end 224 of the conduit 220, where the fluid, drains from the conduit into the intestine or elsewhere in the GI tract. Such capillary action will move the fluid through the elongate conduit 220 when a patient is in any position and in certain embodiments movement of fluid through the elongate conduit 220 may not be gravity dependent. In certain embodiments, ribs 228 positioned on the luminal or interior wall of the elongate conduit 220 allow for capillary attraction of fluid through the elongate conduit 220 while keeping the conduit 220 substantially open or patent and preventing complete closure or reducing closure of the elongate conduit 220 on itself during use, e.g., when intestinal contractions are forcing or pushing, the side-walls of the elongate conduit 220 together.

FIGS. 6A-6B show another embodiment of device 200 where the device 200 includes a sheath 230, sleeve or other covering disposed on or around support frame 202. The first end 232 of sheath 230 may be attached to the first cuff 204 and/or the second end 234 of the sheath 230 may be attached to a second cuff 206. A gap 236 or space may be formed between an exterior wall of the central portion 208 of the support frame 202 and the sheath 230. The sheath 230 also includes an opening 238 for receiving fluid directly from one or more duct openings or via a reservoir which is defined by the device cuffs, the exterior wall of the central portion 208 of the support frame 202 or the sheath 230 and a wall of the small intestines. Optionally, the sheath 230 may be attached to the wall of the central portion 208 of the support frame 202. In certain embodiments, no gap or space is formed between the support frame or central portion 208 and the sheath 230 as the two are attached or bonded together, or the sheath is configured to mold to the shape of the support frame. The sheath may be made from a variety of materials. Examples of such materials include but are not limited to polyethylene, polypropylene. PTFE, hydrogels, and polyesther. In certain embodiments, a polyethylene condom is used as a sheath.

In certain embodiments, the sheath 230 may be made from a material that is flexible such that when the device 200 is positioned in the intestine, fluid emptying from the duct may press against the sheath 203, causing the sheath to give or flex allowing, fluid to collect in a space or reservoir formed between the sheath 230, the first and second cuffs 204, 206 and the intestine wall. The flexibility or elasticity of the sheath may vary, thereby varying the size of the space or reservoir, which may also vary depending on the amount or type of fluid emptying from the duct. The opening 238 in the sheath 203 may be fused with the opening 212 in the support frame 202. The opening 238 may be aligned or substantially aligned with the opening 212. Optionally, the openings 238, 212 may not be aligned, e.g., where fluid enters opening 238, fills the gap or space between the sheath and the central portion, and then enters opening 212 Optionally, a bridge or connection tube or conduit may connect the opening 238 and opening 212, such that fluid may pass through the bridge or tube or conduit in order to enter opening 212 and then enter opening 213 of the elongate conduit 220. In certain embodiments, fluid from the duct may collect in or empty into the gap 236 or space between the exterior wall of the central portion 208 of the support frame 202 and the sheath 230, where the fluid may ultimately empty into opening 212 and into opening 213 in the side-wall of the elongate conduit 220 connected thereto such that the fluid flows through lumen 226 and is diverted through elongate conduit 220 where it exits from the second end 224 of the conduit.

In certain embodiments, the opening 238 in the sheath of the device may be aligned or substantially aligned with the duct opening in the intestine in order to receive fluid from the duct when the device is in use. In other embodiments, for example where there is spacing or a reservoir formed between the sheath 230 and the wall of the intestine or in embodiments where the sheath 230 has the ability to give or flex as a result of the force or weight of the fluid from the duct against the sheath 230, the opening 238 may or may not be aligned with the duct opening. The cuffs 204, 206, however, should flank the duct opening such that the cuffs are positioned proximal and distal to the duct opening, creating boundaries of a reservoir. Fluid from the duct may empty and collect into the reservoir before flowing into opening 238 and opening 212, and the openings may be facing toward or away from the duct opening and/or situated above or below the duct opening, but positioned within the reservoir created by the cuffs, thus still permitting fluid to empty into the openings.

In certain embodiments, the support frame 202 may be in the form of a stent structure. The stent structure may be configured to expand against a wall of the GI tract or intestine. The stent structure may include a shape memory alloy. Optionally, the stent structure may be configured such that when it reaches body temperatures it expands against a wall of the GI tract or intestine. The stent may be made from a variety of materials known in the art. Materials used to make the stent may include but are not limited to nitinol and silicone. Optionally, the stent may be coated with silicone.

The support frame 202 may be enclosed, coated or have a tube placed there through to prevent fluids from passing through the wall of the support frame 202 at any location other than the opening 212. For example, the support frame may be coated with silicone and/or include a bioabsorbable material.

Figure 9:
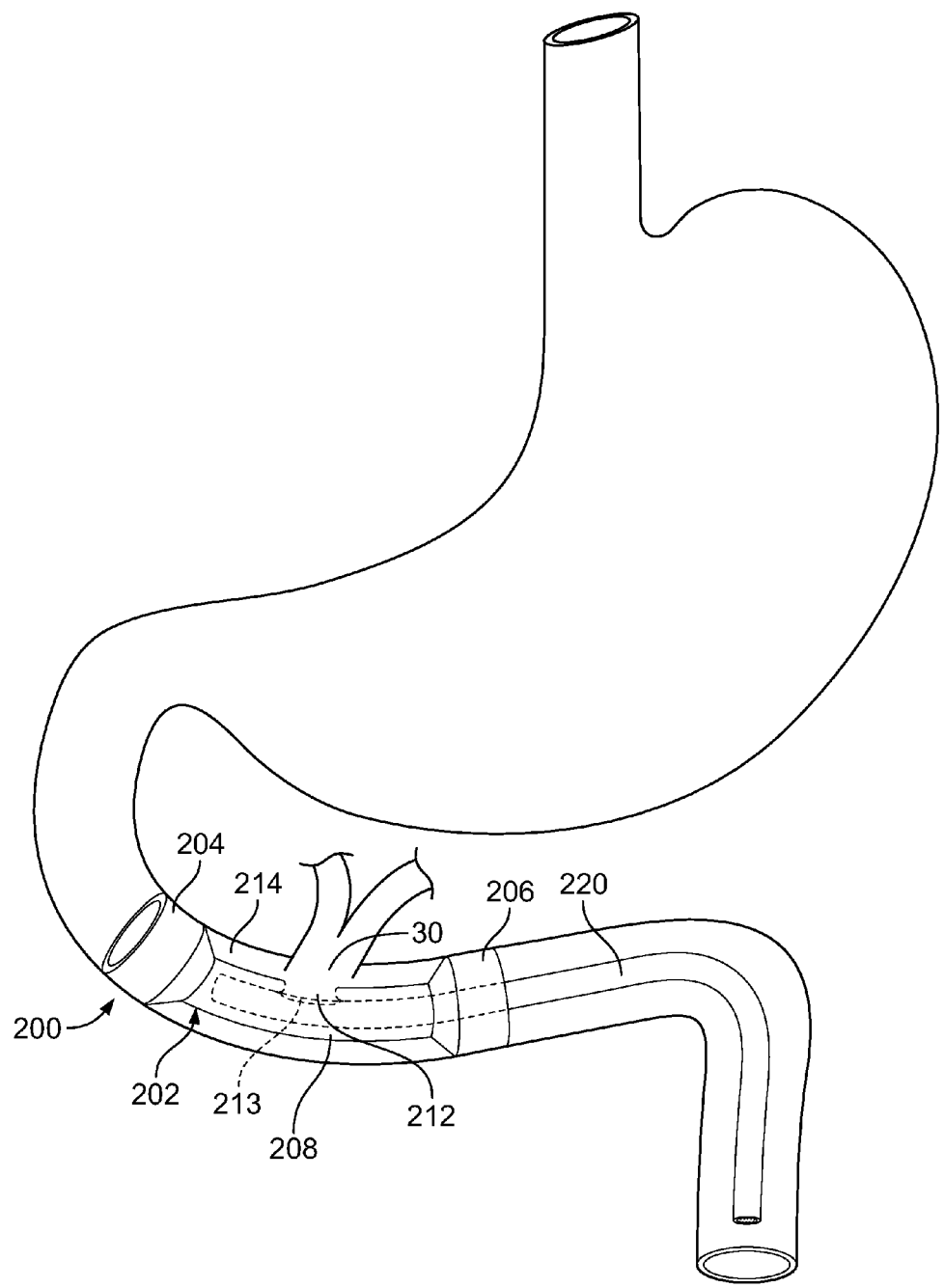
FIG. 9. illustrate a variation of a gastrointestinal device placed in the small intestine.

FIG. 9. illustrates one example of the gastrointestinal device 200 in use, where the device is placed in the small intestine. The devices described herein may be placed in the small intestines or anywhere in the GI tract or other pathways in the body where the bypass or diversion or rerouting of fluids, solids, or bodily substances from one section of a pathway to another is desired. The device 200 may be placed in the small intestines or other bodily pathway using a variety of delivery mechanisms. The device 200 may be mounted on a delivery catheter and/or a scope may be used for delivery. The device 200 may be placed with the use of a balloon or other expansion mechanism. Alternatively, the device 200 may self-expand to fit within the pathway, e.g., within the small intestine 20. Fluid may be used to deploy the second end 224 of the elongate conduit 220 distally in the small intestine 20. The elongate conduit 220 may also self-deploy over time.

A method for diverting or bypassing, or rerouting fluid from a duct in a wall of the GI tract according to one embodiment includes inserting a device 200 into the small intestine. The device 200 includes a support frame 202 which has a first cuff 204, a second cuff 206, and a central portion 208 defining, a passageway 210 which may extend between the first and second cuffs 204, 206. The central portion 208 may have a reduced diameter relative to a diameter of the first or second cuffs 204, 206. The central portion 208 also has one or more openings 212 in a side-wall of the central portion 208. An elongate conduit 220 is coupled to the side-wall of the central portion 208 and at least a portion of the conduit 220 extends within the passageway 210. The conduit 220 may have a first end 222, a second end 224 having one or more openings, a side-wall having one or more openings 213 and the elongate conduit may have a lumen 226. The opening 213 in the side-wall of the conduit may be directly or indirectly connected, coupled, or otherwise secured, e.g., in fluid communication, to the opening 212 in the side-wall of the support frame 202 or the central portion 208 such that fluid enters the opening 212 and passes through the opening 213 in the side-wall of the conduit 220 and into the conduit lumen 226 where it ultimately exits from the second end 224.

The device 200 may be positioned within the small intestine such that the second cuff 206 is located distal to a duct opening 30 and the first cuff 204 is located proximal to the duct opening 30. In FIG. 9, the duct opening shown is the Ampula of Vater 30. Pancreatic enzymes and/or bile normally pass from the pancreatic duct and/or bile duct and empty from the Ampula of Vater into the intestines.

Once the device 200 is in position in the small intestine, relative to the duct opening, the first and/or second cuffs 204, 206 are expanded against the wall of the small intestines. As a result, the second cuff 206 forms a seal or fluid tight seal against the wall of the small intestines distal to the duct opening and/or the first cuff 204 forms a seal or fluid tight seal against the wall of the small intestine proximal to the duct opening. The first and second cuffs 204, 206 in combination with an exterior wall of the central portion 208 and a wall of the small intestines define a reservoir 214, which is in position to receive fluid from the duct and duct opening.

After expansion of the cuffs, the device 200 is securely positioned within the small intestines with the first and second cuffs 204, 206 of the device being securely positioned against the wall of the small intestines on either side of the duct opening. As such, fluid may be diverted or passed directly from the duct opening or lion) the reservoir 214 through the opening 212 in the side-wall of the central portion 208 of the support frame 202 and through the opening 213 in the side-wall of the conduit 220. Fluid then passes or is advanced from the opening 213 in the side-wall of the conduit 220, through the conduit lumen 226, and drains or exits out of an opening at the second end 224 of the conduit 220. The second end 224 may be positioned within the small intestines at a distance from or a distance distal to the opening 213 and/or the first end 224 and/or the opening 212. Optionally, fluid may be advanced from the first end 222 of the conduit 220 through the conduit and out the second end 224. Fluid, e.g., enzymatic or other bodily fluid, is thereby diverted or rerouted from the duct to a location distal to the duct opening or downstream within the small intestines or GI tract. As a result, the fluid bypasses a portion of the small intestines thereby modifying the location at which fluids from the duct, e.g., enzymatic and other bodily fluids, interact with nutrients from food and food fluids passing through the small intestines and GI tract.

A diameter of the conduit 220 may be smaller than a diameter of the passageway 210, thereby allowing foods, food fluids and other digestive substances to pass through the passageway 210 of the central portion 208 of the device 200 and past the conduit 220, without entering the conduit 220 (or at least minimizing the amount of substance that enters the conduit) while the device 200 is in position in the small intestines.

The device 200 according to any of the embodiments described above is configured such that precise or exact alignment of the opening 212 with the duct opening in order for fluid to pass from the duct to the conduit 220 and be adequately diverted to a different region of the small intestines or GI tract is not required. Because the device 200, when properly positioned with the cuffs situated proximal and distal to the duct opening, forms a reservoir between the device 200 and the intestine wall, duct fluid will be constrained within the reservoir and then diverted into opening 212 by flowing from the reservoir into the opening 212 even when the opening 212 is not aligned with the duct opening. Indeed, depending on how device 200 is rotated within the small intestines or GI tract, opening 212 may be facing toward or away from the duct opening or positioned above or below the duct opening or facing in any number of other directions relative to the duct opening. In any of these configurations, fluid may still make its way from the duct opening, into the device opening 212, through opening 213 in the side-wall of the conduit 220 and into the conduit 220, e.g., via the reservoir 214. Thus, these features allow the device 200 to be properly placed in the GI tract or small intestine with ease and with reduced concern or sensitivity regarding where opening 212 and/or opening 238 (in certain embodiments utilizing a sheath 230) is positioned relative to a duct opening.

In certain embodiments, the support structure 202 or cuffs 204, 206 may be fastened, secured, or attached to the wall of the intestines by a variety of mechanisms. For example, the device 200 and/or cuffs may be friction fit against the wall of the small intestines such that the device won't dislodge once in place. The device 200 may be removable or reversible, such that the device 200 can be removed from a patient at any time, e.g., after desired or positive results in a patient are achieved, such as improved health or weight loss.

The length of the conduit 220 may vary depending on the particular patient and the desired treatment. The conduit 220 may be adjustable. For example, the length of the conduit 220 may be adjusted, shortened or lengthened to modify the location at which fluid from the duct drains from the second end 224 of the conduit 220 and interacts with food or food fluids in the small intestine. Accordingly, the length may be adjusted such that it is sufficient to limit the interaction of fluid from the duct with food product or food fluids to the extent necessary to adequately and successfully treat a patient.

As stated supra, the device 200 may be placed in the small intestines using a variety of delivery mechanisms or devices. In certain embodiments, the device 200 may be located on a balloon catheter, and the balloon may be inflated to expand the device 200 within the intestine. In other embodiments, the device 200 may be located on a catheter and restrained in a delivery or collapsed state, where the device is expanded by unrestraining the device 200. It is also contemplated that device 200 may be modified or combined with any of the features or elements or embodiments described or illustrated in the embodiments of FIGS. 1-4, above.

In addition to assisting in controlling, obesity, the implants or devices described herein may also be used to aid in the treatment or management of Metabolic Syndrome, which includes various conditions such as diabetes, hypertension, hypercholesterolemia, and increased waist circumference. For example, placement of the implants in patients with diabetes may serve to reduce glucose intolerance and/or insulin resistance by bypassing fluids within the bowels in the manner described above and aid in diabetes treatment or management.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims. Furthermore, the above illustrations are examples of the invention described herein. Because of the scope of the invention, it is specifically contemplated that combinations of aspects of specific embodiments or combinations of the specific embodiments themselves are within the scope of this disclosure.

What is claimed is:

1. A device for diverting fluid from a duct in a wall of a small intestine, the device comprising:
    a support frame having a first cuff, a second cuff, a central portion and a passageway extending through the central portion, where the central portion has a reduced diameter relative to a diameter of the first or second cuffs and at least one opening in a side-wall of the central portion, wherein the first and second cuffs are expandable, the second cuff being configured to form a fluid tight seal against the wall of the small intestine distal to a duct opening and the first cuff being configured to form a fluid tight seal against the wall of the small intestine proximal to the duct opening such that the first and second cuffs in combination with an exterior wall of the central portion and a wall of the small intestine define a reservoir for receiving fluid from the duct; and
    an elongate conduit coupled to the side-wall of the central portion where at least a portion of the conduit extends within the passageway is bonded to an interior wall of the central portion of the support frame, the conduit having a first end, a second end having an opening, and a side-wall having an opening, wherein the opening in the side-wall of the conduit is connected to the opening in the side-wall of the central portion such that fluid entering the opening in the side-wall of the central portion from the reservoir or directly from the duct passes through the opening in the side-wall of the conduit, the conduit being configured to advance fluid from the opening in the side-wall of the conduit to the second end of the conduit and, wherein a diameter of the elongate conduit is smaller than a diameter of the passageway such that foods and other digestive substances may pass through the passageway and past the conduit without entering the conduit.

2. The device of claim 1, wherein the first end of the conduit is positioned proximal to the opening in the side-wall of the central portion of the support frame.

3. The device of claim 1, wherein the second end of the conduit is positioned within the small intestine at a distance from the opening in the side-wall of the conduit.

4. The device of claim 3, wherein a, plurality of ribs are positioned along a longitudinal length of an interior wall of the conduit, the ribs extending toward a central axis of the conduit.

5. The device of claim 1, wherein the portion of the conduit extending within the passageway of the central portion of the support frame is bonded to an interior wall of the central portion of the support frame.

6. The device of claim 1, wherein the conduit comprises at least one rib on an interior wall of the conduit to prevent the conduit from completely closing on itself.

7. The device of claim 1, wherein the device further comprises a sheath disposed
around the support frame, where a first end of the sheath is attached to a first cuff and a second end of the sheath is attached to a second cuff creating a gap between an exterior wall of the central portion and the sheath, the sheath having an opening for receiving fluid from the duct.

8. The device of claim 1, wherein the conduit is length adjustable.

9. The device of claim 1, wherein the conduit is flexible and comprises a polymer
selected from the group consisting of thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

10. The device of claim 1, where the support frame has a stent structure and the stent structure comprises a shape memory alloy, and where the stent structure is configured to expand against a wall of the small intestine.

11. The device of claim 1, wherein the support frame is coated with silicone.

12. The device of claim 1, where the support frame comprises a bioabsorbable material.

13. The device of claim 1, where the conduit comprises a bioabsorbable material.

14. A method for diverting fluid from a duct in a wall of a small intestine, the method comprising;
inserting a device into the small intestine, the device comprising a support frame having a first cuff, a second cuff, a central portion and a passageway extending through the central portion where the central portion has a reduced diameter relative to a diameter of the first or second cuffs and at least one opening in a side-wall of the central portion, and an elongate conduit coupled to the side-wall of the central portion where at least a portion of the conduit extends within the passageway and a diameter of the conduit is smaller than a diameter of the passageway, the conduit having a first end, a second end having an opening, and a side-wall having an opening, wherein the opening in the side-wall of the conduit is connected to the opening in the side-wall of the central portion such that fluid entering the opening in the side-wall of the central portion passes through the opening in the side-wall of the conduit;
a sheath disposed around the support frame, where a first end of the sheath is attached to a first cuff and a second end of the sheath is attached to a second cuff creating a gap between an exterior wall of the central portion and the sheath, the Sheath having an opening for receiving fluid from the duct;
positioning, the device within the small intestine such that the second cuff is located distal to a duct opening and the first cuff is located proximal to the duct opening;
expanding the first and second cuffs against the wall of the small intestine such that the second cuff forms a fluid tight seal against the wall of the small intestine distal to the duct opening and the first cuff forms a fluid tight seal against the wall of the small intestine proximal to the duct opening, such that the first and second cuffs in combination with an exterior wall of the central portion and a wall of the small intestine define a reservoir for receiving fluid from the duct;
diverting fluid from the reservoir or directly from the duct opening through the opening in the side-wall of the central portion and through the opening in the side-wall of the conduit, where the fluid is advanced from the opening, in the side-wall of the conduit to the second end of the conduit positioned within the small intestine at a distance from the opening in the side-wall of the conduit; and
allowing foods and other digestive substances to pass through the passageway and past the conduit without entering the conduit.

15. The method of claim 14, wherein the duct opening is an opening of an Ampula of Vater.

16. The method of claim 14, wherein the conduit comprises a length sufficient to limit the interaction of fluid from the duct with food product.

17. The method of claim 16, wherein the length of the conduit is adjusted to modify the location at which fluid from the duct drains from the second end of the conduit and interacts with food in the small intestine.

18. The method of claim 14, where the device is located on a balloon catheter, and further comprising inflating the balloon to expand the support frame.

19. The method of claim 14, where the device is located on a catheter an restrained
in a delivery state and where expanding the device comprises unrestraining the support frame.

20. The method of claim 14, wherein the conduit comprises at least one rib on an interior wall of the conduit to prevent the conduit from completely closing on itself.

21. The method of claim 14, wherein the conduit is flexible and comprises a polymer
selected from the group consisting of thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

22. The method of claim 14, wherein fluid is diverted from a duct in a wall of a small intestine to manage Metabolic Syndrome.

23. The method of claim 14, wherein fluid is diverted from a duct in a wall of a small intestine to manage Diabetes.

24. A device for diverting fluid from a duct in a wall of a small intestine, the device comprising:
a support frame having a first cuff a second cuff, a central portion and a passageway extending through the central portion, where the central portion has a reduced diameter relative to a diameter of the first or second cuffs and at least one opening in a side-wall of the central portion, wherein the first and second cuffs are expandable, the second cuff being configured to form a fluid tight seal against the wall of the small intestine distal to a duct opening and the first cuff being, configured to form a fluid tight seal against the wall of the small intestine proximal to the duct opening such that the first and second cuffs in combination with an exterior wall of the central portion and a wall of the small intestine define a reservoir for receiving fluid from the duct; and an elongate conduit coupled to the side-wall of the central portion where at least a portion of the conduit extends within the passageway, the conduit having a first end, a second end having an opening, and a side-wall having an opening, wherein the opening in the side-wall of the conduit is connected to the opening in the side-wall of the central portion such that fluid entering the opening in the side-wall of the central portion from the reservoir or directly from the duct passes through the opening in the side-wall of the conduit, the conduit being configured to advance fluid from the opening in the side-wall of the conduit to the second end of the conduit and, wherein a diameter of the elongate conduit is smaller than a diameter of the passageway such that foods and other digestive substances may pass through the passageway and past the conduit without entering the conduit; and a sheath disposed around the support frame, where a first end of the sheath is attached to a first cuff and a second end of the sheath is attached to a second cuff creating a gap between an exterior wall of the central portion and the sheath, the sheath having an opening for receiving fluid from the duct.

\* \* \* \* \*